United States Patent
Haarala et al.

(10) Patent No.: US 7,182,746 B2
(45) Date of Patent: Feb. 27, 2007

(54) REVERSIBLE LUMEN CATHETER

(75) Inventors: Brett Haarala, Framingham, MA (US); Robert Frechette, Lakeville, MA (US); Kurt Haggstrom, Plainville, MA (US); Scott MacMeans, Attleboro, MA (US); Elise Tordella, Norfolk, MA (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 11/060,469

(22) Filed: Feb. 11, 2005

(65) Prior Publication Data

US 2005/0267400 A1   Dec. 1, 2005

Related U.S. Application Data

(63) Continuation-in-part of application No. 10/602,897, filed on Jun. 24, 2003, now Pat. No. 7,141,035, which is a continuation-in-part of application No. PCT/US03/09687, filed on Mar. 28, 2003.

(60) Provisional application No. 60/543,623, filed on Feb. 11, 2004.

(51) Int. Cl.
*A61M 3/00* (2006.01)
(52) U.S. Cl. .......................... 604/43; 604/32
(58) Field of Classification Search ............... 604/39, 604/43, 44, 523, 533, 905, 6.1, 30, 32
See application file for complete search history.

(56) References Cited

U.S. PATENT DOCUMENTS

| | | | |
|---|---|---|---|
| 3,973,592 A | 8/1976 | Cleaver et al. ........ 137/625.43 |
| 4,551,130 A * | 11/1985 | Herbert et al. ................ 604/32 |
| 4,701,159 A * | 10/1987 | Brown et al. ................. 604/43 |
| 5,569,182 A | 10/1996 | Twardowski et al. ......... 604/43 |
| 6,319,465 B1 * | 11/2001 | Schnell et al. ................ 422/44 |
| 6,596,234 B1 | 7/2003 | Schnell et al. ................ 422/44 |
| 6,638,242 B2 * | 10/2003 | Wilson et al. ................ 604/43 |
| 6,786,884 B1 * | 9/2004 | DeCant et al. ................ 604/43 |
| 2002/0099327 A1 | 7/2002 | Wilson et al. ................ 604/43 |
| 2003/0018290 A1 | 1/2003 | Brugger et al. .............. 604/6.1 |

FOREIGN PATENT DOCUMENTS

WO   WO 03/033049 A2   4/2003

* cited by examiner

*Primary Examiner*—Nicholas Lucchesi
*Assistant Examiner*—Theodore J. Stigell
(74) *Attorney, Agent, or Firm*—Carter, DeLuca, Farrell & Schmidt, LLP

(57) ABSTRACT

A catheter is provided including a tubular body having a proximal end and a distal end. The body includes a first lumen and a second lumen with a septum disposed therebetween. The proximal end includes a valve and a hub that are integral with the body. The hub includes a first conduit and a second conduit. The valve includes a first port and a second port that are rotatable, about a longitudinal axis of the body, to establish fluid communication between the lumens and the conduits. The distal end of the tubular body may be configured for insertion with a subject. The conduits may be connectable to a medical apparatus.

12 Claims, 26 Drawing Sheets

REVERSIBLE LUMEN CATHETER

RELATED APPLICATION INFORMATION

This patent application claims the benefit of U.S. Provisional Application No. 60/543,623 filed by Haarala et al. on Feb. 11, 2004 and is a continuation-in-part of U.S. application Ser. No. 10/602,897 filed on Jun. 24, 2003 now a U.S. Pat. No. 7,141,035, which is a continuation-in-part of PCT International Application Serial No. PCT/US03/09687, filed on Mar. 28, 2003 designating the United States of America, the entire contents of these documents being incorporated herein by reference.

BACKGROUND

1. Technical Field

The present disclosure generally relates to medical catheter apparatus and, more particularly, to a catheter that facilitates bi-directional fluid flow and resolves occlusion during use.

2. Description of the Related Art

Some known catheters are tubular, flexible medical devices for administration of fluids (withdrawal, introduction, etc.) with cavities, ducts, vessels, etc. of a body. Typically, catheter devices are inserted with the cavity of a body via a sheath, stylet, trocar, etc.

These catheter devices may be employed for administration of fluids that includes the simultaneous introduction and withdrawal of fluid for applications such as, surgery, treatment, diagnosis, etc. In one particular hemodialysis application, blood is withdrawn from a blood vessel for treatment by an artificial kidney device and the treated blood is introduced back into the blood vessel.

Various known catheter devices have been employed for simultaneous withdrawal and introduction of fluid with a body. Some devices utilize multiple lumens, such as dual lumen catheters that facilitate bi-directional fluid flow whereby one lumen is dedicated for performing withdrawal of blood and the other lumen is dedicated for introducing treated blood to the vessel. During an exemplary hemodialysis procedure, a multiple lumen catheter is inserted into a body and blood is withdrawn through an arterial lumen of the catheter. This blood is supplied to a hemodialysis unit which dialyzes, or cleans, the blood to remove waste and excess water. The dialyzed blood is returned to the patient through a venous lumen of the catheter. Typically, the venous lumen is separated from the arterial lumen by an inner catheter wall, called a septum.

Typically the arterial lumen is located upstream (closer to the heart of the body) from the venous lumen to ensure that the processed blood is not recirculated immediately back to the hemodialysis unit. Recirculation of blood flow occurs when the dialyzed blood exiting the venous lumen is directly returned to the arterial lumen. The more blood that does immediately recirculate, the less efficient the hemodialysis procedure.

Another complication of hemodialysis catheters is flow occlusion. Common causes of occlusion are fibrin sheath formation, thrombus formation and positional occlusion. Flow occlusion is primarily caused by blockage of the arterial lumen. Resolving poor flow is required to deliver the dialysis treatment to the patient. Current measures taken to resolve flow occlusion, include repositioning the patient, flushing the lumens and reversing the blood lines of the catheter to the hemodialysis unit.

With positional occlusion of the catheter, there can be difficulty in removing blood from the patient. For example, a tip of the catheter has, to some extent, freedom of movement inside the patient, and this can cause occlusion. As a result, the clinician must resolve any interruption in flow to allow continuance of patient treatment. One solution for resolving positional occlusion of blood flow is to reverse flow of the lumens of the catheter at the associated blood line of the hemodialysis unit, which withdraws and introduces blood flow using a pump. This allows the treatment to continue, however, the amount of recirculated blood is increased. Changing flow on current catheters involves decoupling and recoupling the lines, increases clinician handling of the catheter and increases the opportunity for microbial contamination and infection, as well as extending the time of the dialysis treatment. This results in various drawbacks including increased cost and discomfort for the patient.

Therefore, it would be desirable to overcome the disadvantages and drawbacks of the prior art with a catheter that employs a tubular body having an integral hub and a valve that facilitates bi-directional fluid flow to resolve occlusion. It would be desirable if the integral hub is manipulable to rotate the valve such that fluid flow in the body of the catheter is reversible. It would be highly desirable if the valve is releasably lockable with the tubular body to facilitate fluid flow and achieve the principles of the present disclosure. It is contemplated that the catheter and its constituent parts are easily and efficiently manufactured and assembled.

SUMMARY

Accordingly, a catheter is provided that employs a tubular body having an integral hub and a valve that facilitates bi-directional fluid flow to resolve occlusion for overcoming the disadvantages and drawbacks of the prior art. Desirably, the integral hub is manipulable to rotate the valve such that fluid flow in the body of the catheter is reversible. Most desirably, the valve is releasably lockable with the tubular body to facilitate fluid flow and achieve the principles of the present disclosure. The catheter is easily and efficiently manufactured and assembled. The present disclosure resolves related disadvantages and drawbacks experienced in the art.

The catheter allows quick and effective reversal of the fluid flow without having to recouple the fluid connections. The catheter allows the clinician to quickly reverse the flow of the blood in the lumens without disconnecting and reconnecting in the wrong configuration. Also, since the catheter tip may have a symmetrical tip geometry so that there is no loss of efficiency due to reversal of the lumens. No additional external devices are required. In addition, flow may be reversed as a preventive measure to minimize build up of thrombus at the arterial lumen. The present disclosure benefits from many advantages including sealing ability, long term durability, compatibility with blood and chemical environment, ease of usage, durability of assembly and size of hub.

The present catheter design includes an integral hub that can readily switch the fluid path from a hemodialysis unit. In one particular embodiment, the catheter includes a proximal end having a spring-assisted rotating seal. Switching of the flow is enabled by a rotating sleeve, which in turn rotates the catheter fluid connections relative to the catheter lumens.

In an alternative embodiment, the spring is eliminated and a set distance of compression for an elastic sealing system is employed. The present disclosure orients the fluid seals to ensure flow is directed into the respective lumen as well lock the orientation into position. Direction of fluid flow may be facilitated by convex and concave mating surfaces that flexibly deform with rotational forces, or alternatively a ball/spring type ratchet device, which mates with a depressed surface, may be used. The present disclosure contemplates a visual indicia of proper orientation of the lumens so the clinician is aware that it is acceptable to resume flow. Audible and tactile feedback are also envisioned.

The catheter may also seal the lumens closed as a result of rotation and/or changes in lumen flow. It is envisioned that this configuration may apply to a single lumen catheter. The lumens may include open areas that are approximately 90° sections opposed across a center axis. When aligned, the flow is allowed across the openings to the aligned path. When rotated 90°, the flow is stopped and the access is sealed. When rotated 90° in the same direction, the opposite lumens are aligned, reversing the original alignment. When rotated the final 90° the catheter access is again sealed.

The catheter may include rotating parts that are locked in place so the catheter can be selectively positioned. Visual markings to indicate the orientation are also desired. In another embodiment, the catheter includes a selectively detachable assembly. The rotatable or moveable sealing members may be connected and disconnected to an indwelling catheter by any type of fluid connection method, including connection to a hub or directly connecting to a catheter with mating connection to the lumens.

In a method for using a reversible catheter to resolve flow malfunction is provided. Occlusion of the catheter lumen during hemodialysis is often caused by thrombus or fibrin interfering with the flow on the arterial (or venous) lumen. Such material may build up over the course of several dialysis sessions, or in dwelling in a vein for an extended amount of time. Thus, reversing the lumens of the dialysis catheter can resolve the occlusion of some cases by blowing the material away from the lumen when flow is reversed. Visual indicia, as disclosed herein, indicate direction of flow to resolve many issues of flow malfunction in hemodialysis catheter access. In an alternate embodiment, a method for using a reversible catheter to prevent flow malfunction is provided. This method involves steps to prophylatically switch the flow of the catheter to eliminate a build up by blowing it off or dissolving it from the intake lumen before it can severely restrict flow. This method instructs the operators of the catheter in dialysis to reverse the lumens of the catheter periodically, prior to each treatment for example.

In another embodiment, the principles of the present disclosure may be employed with symmetrical catheters, whereby the lumens are substantially similar in dimension and configuration. It is contemplated that recirculation would be limited to <5%.

In one particular embodiment, in accordance with the principles of the present disclosure a catheter is provided including a tubular body having a proximal end and a distal end. The body includes a first lumen and a second lumen with a septum disposed therebetween. The proximal end includes a valve and a hub that are integral with the body. The hub includes a first conduit and a second conduit. The valve includes a first port and a second port that are rotatable, about a longitudinal axis of the body, to establish fluid communication between the lumens and the conduits. The distal end of the tubular body may be configured for insertion with a subject. The conduits may be connectable to a medical apparatus.

The hub may be connected with the valve such that rotation of the hub causes corresponding rotation of the ports. The first port can be aligned with the first conduit and the second port aligned with the second conduit. The first port and the second port may have a sector configuration. The valve may be rotatable to a first position, such that the first port is aligned with the first lumen and the second port is aligned with the second lumen, and a second position, such that the first port is aligned with the second lumen and the second port is aligned with the first lumen. The valve maybe rotatable to a third position, such that the ports are not aligned with the lumens and fluid communication between the conduits and the lumens is prevented.

The valve may be releasably lockable with the tubular body in the first position and the second position. Alternatively, the catheter includes a locking member that fixes the valve with the body to prevent rotation thereof. The locking member can be biased to fix the valve with the body and prevent rotation thereof. The locking member can be axially manipulable to release the valve from locking engagement with the body for corresponding rotation.

The proximal end of the catheter may includes visual indicia of the position of the valve. Alternatively, the proximal end includes a first lumen opening and a second lumen opening formed in a proximal face of the body. The proximal end may further include an integral hub having a valve, the valve including a washer configured for engagement with the proximal face of the body and the hub including a first conduit that extends to a first port of the valve and a second conduit that extends to a second port of the valve, the washer having non-circular openings configured for disposal about the ports of the valve. The hub can be manipulable to rotate the first port and the second port, about a longitudinal axis of the body, to establish fluid communication between the lumens and the conduits. Thus, the ports are releasably fixable in alignment with the first and second lumen openings during fluid communication.

The locking member may releasably fix the valve with the proximal face for alignment of the ports with the first and second lumen openings. The locking member may include a projection of the hub configured for disposal within a cavity disposed adjacent the proximal face. The locking member may include a sleeve connected with the hub and is movable relative to the body. The sleeve includes a projection configured for disposal within a cavity disposed adjacent the proximal face to fix alignment. The sleeve can be biased to fix the valve with the proximal face. The sleeve may further include a radially inward projecting tab configured for disposal within a groove of the hub to facilitate rotation of the ports independent of the lumen openings.

In another alternate embodiment, the catheter includes a tubular body having a proximal end and a distal end configured for connection to a subject. The body includes a first lumen and a second lumen with a septum disposed therebetween. The tubular body further includes a first wall that defines the first lumen and a second wall that defines the second lumen. A portion of the septum extending distally beyond the first lumen and the second lumen such that the first wall includes a first wall extension that extends in a spiral configuration from the first lumen and is spaced apart from the portion of the septum.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, as set forth below.

DETAILED DESCRIPTION OF EXEMPLARY EMBODIMENTS

Figure 1:
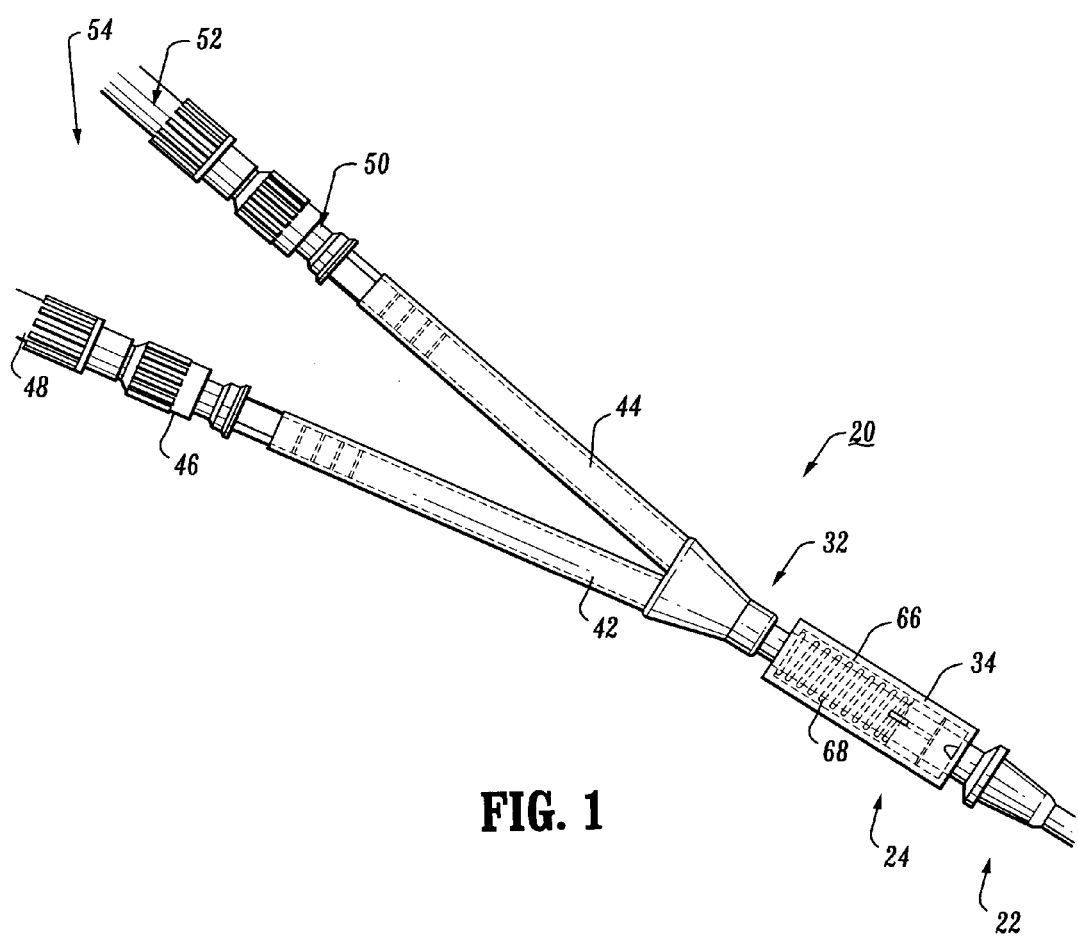
FIG. 1 is a perspective view of a catheter, in accordance with the principles of the present disclosure.

The exemplary embodiments of the catheter and methods of use disclosed are discussed in terms of medical catheters for the administration of fluids (withdrawal, introduction, etc.) with the body of a subject and more particularly, in terms of a catheter that employs a tubular body having an integral hub and a valve that facilitates bi-directional fluid flow to resolve occlusion. The catheter may also employ bi-directional fluid flow to prevent occlusion. It is envisioned that the present disclosure may be employed with a range of catheter applications including surgical, diagnostic and related treatments of diseases, body ailments, etc. of a subject. It is further envisioned that the principles relating to the catheter disclosed include employment with various catheter related procedures, such as, for example, hemodialysis, cardiac, abdominal, urinary, intestinal, etc., in chronic, acute, etc. applications. It is contemplated that the catheter can be used for administration of fluids such as, for example, medication, saline, bodily fluids such as, blood, urine, etc.

In the discussion that follows, the term "proximal" will refer to the portion of a structure that is closer to a practitioner, while the term "distal" will refer to the portion that is further from the practitioner. As used herein, the term "subject" refers to a human patient or other animal. According to the present disclosure, the term "practitioner" refers to a doctor, nurse or other care provider and may include support personnel.

The following discussion includes a description of the catheter, followed by a description of an exemplary method of operating the catheter in accordance with the principles of the present disclosure. Alternate embodiments are also disclosed. Reference will now be made in detail to the exemplary embodiments of the present disclosure, which are illustrated in the accompanying figures. Turning now to the figures wherein like components are designated by like reference numerals throughout the several views and initially to FIGS. 1–3, there is illustrated a medical device, such as, for example, a catheter 20, in accordance with the principles of the present disclosure.

The components of catheter 20 are fabricated from materials suitable for medical applications, such as, for example, polymerics or metals, such as titanium, stainless steel, depending on the particular catheter application and/or preference of a practitioner. Semi-rigid and rigid polymerics are contemplated for fabrication, as well as resilient materials, such as molded medical grade polyurethane, silicone, etc. The sealing components of catheter 20 may be fabricated from low friction property materials such as, polytetrafluoroethylene (PTFE) coated, PTFE impregnated, internally lubricated elastomers, etc. One skilled in the art, however, will realize that other materials and fabrication methods suitable for assembly and manufacture, in accordance with the present disclosure, also would be appropriate.

Catheter 20 is reusable in a catheter application such as, for example, a hemodialysis treatment. Therefore, catheter 20 can be employed for multiple treatments. This advantageous configuration is convenient and reduces cost. It is contemplated that catheter 20 may be configured for catheter applications employing one or a plurality of lumens. It is envisioned that catheter may also be used in disposable applications.

Catheter 20 includes a tubular body 22 having a proximal end 24 and a distal end (not shown). The distal end is configured for insertion within a body cavity, such as, for example, a blood vessel. It is contemplated that the distal end of tubular body 22 may have a split tip configuration, staggered, etc. The distal end may employ a guidewire, sheath, trocar, etc. to facilitate disposal of tubular body 22 within the blood vessel.

Tubular body 22 is elongated and has a cylindrical outer surface. It is contemplated that tubular body 22 may be variously dimensioned and attachable to other medical devices. It is further contemplated that the outer surface of tubular body 22 may have various configurations, such as, for example, rectangular, elliptical, polygonal, etc. It is envisioned that tubular body 22 may have an attached cuff or the like for subcutaneous in growth of tissue for securement of catheter 20. Tubular body 22 may include sideholes. For example, the distal end of tubular body 22 may include lateral openings and/or slots.

Figure 2:
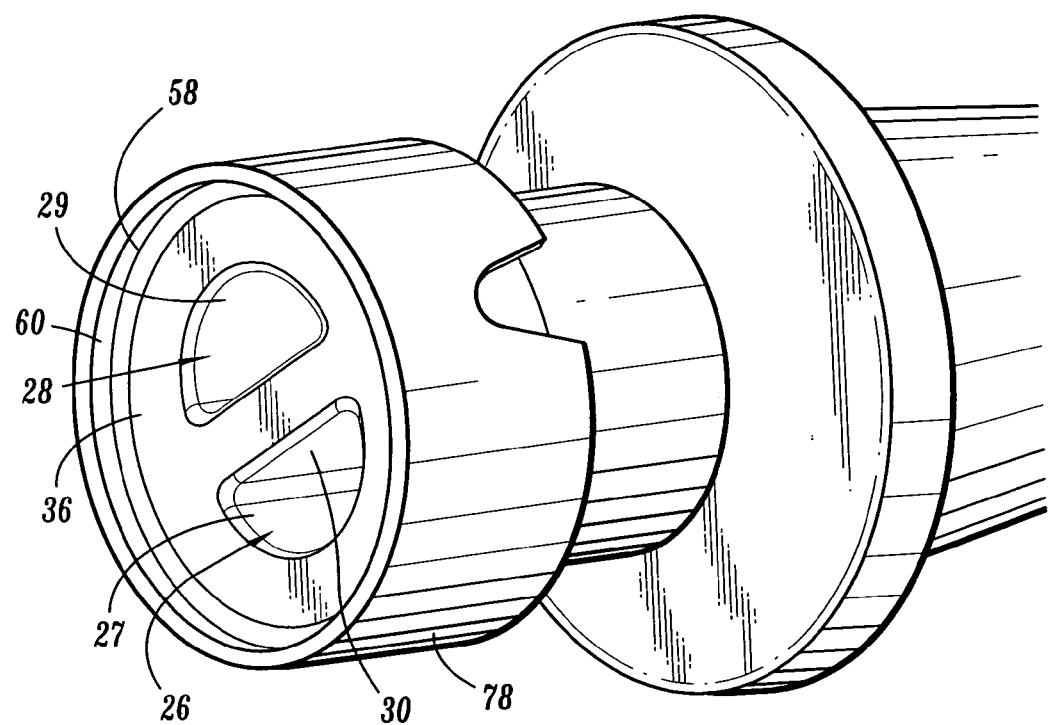
FIG. 2 is a perspective view of a distal end of a tubular body of the catheter shown in FIG. 1.

Tubular body 22 defines a first lumen such as, for example, venous lumen 26 and a second lumen such as, for example, arterial lumen 28 with a septum 30 disposed therebetween. Venous lumen 26 and arterial lumen 28 each have a substantially D-shaped or semi-circular configuration, as shown in FIG. 2. Venous lumen 26 includes an inner surface 27 having a substantially planar portion and a substantially arcuate portion. Arterial lumen 28 similarly includes an inner surface 29 having a planar portion and an arcuate portion.

Figure 4:
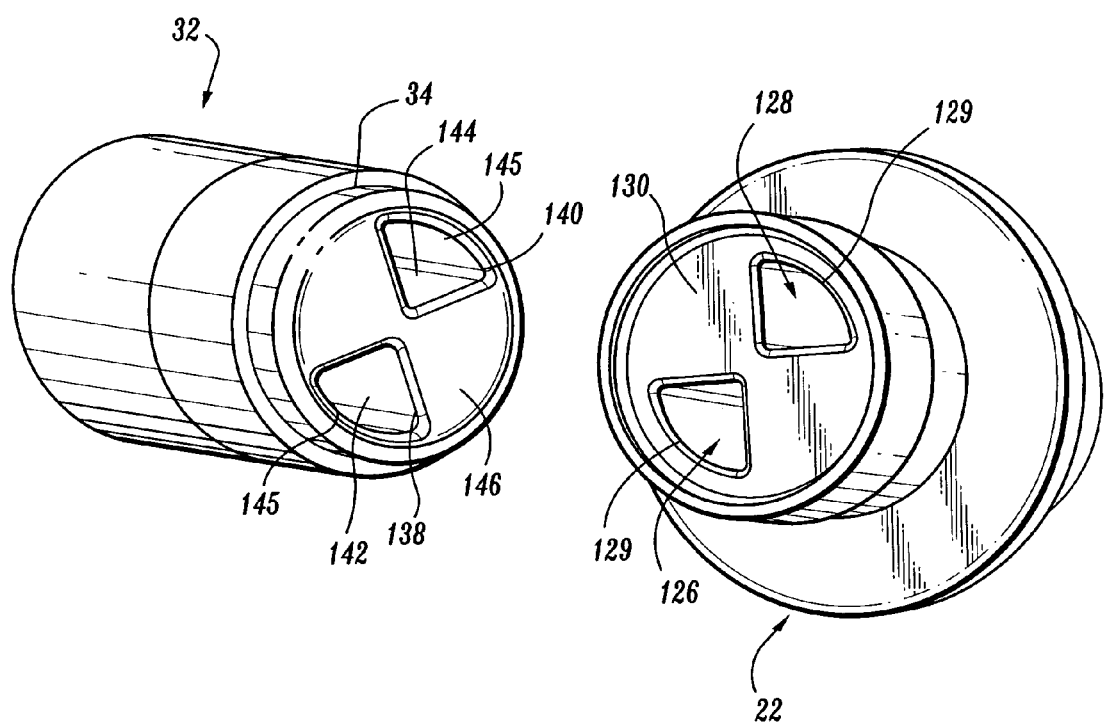
FIG. 4 is a perspective view of an alternate embodiment of the hub, valve and body shown in FIGS. 2 and 3.
Figure 5:
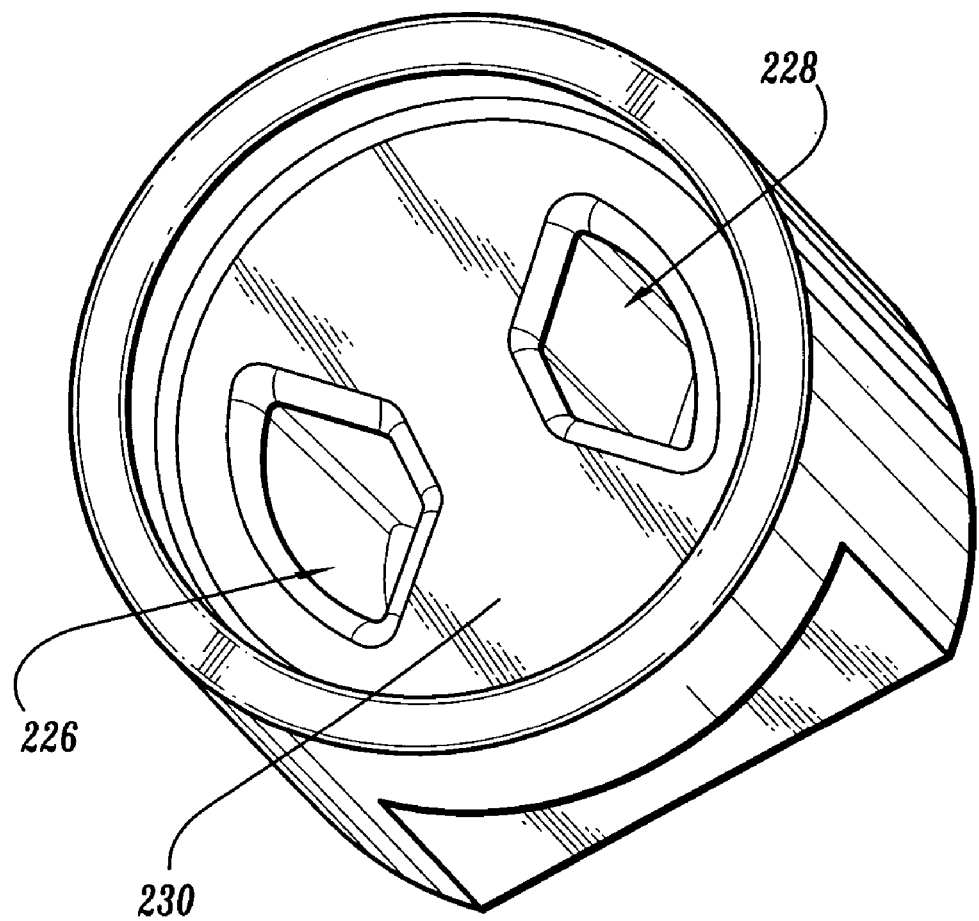
FIG. 5 is a perspective view of an alternate embodiment at the distal end of the tubular body shown in FIG. 2.

Lumens 26, 28 are elongated with tubular body 22 and inner surfaces 27, 29 are configured to facilitate fluid flow within lumens 26, 28. It is envisioned that lumens 26, 28 may have various configurations, such as, for example, cylindrical, rectangular, elliptical, polygonal, etc. For example, in an alternate embodiment as shown in FIG. 4, tubular body 22 includes a venous lumen 126 and an arterial lumen 128 having substantially triangular cross-sections. The triangular cross-sections include arcuate legs 129 and lumens 126, 128 are separated by a central portion 130. In another alternate embodiment as shown in FIG. 5, tubular body 22 includes a venous lumen 226 and an arterial lumen 228 having sector configurations and are separated by a central portion 230.

Venous lumen 26 is configured for fluid flow, such as, for example, venous blood flow, to return blood to a subject. Arterial lumen 28 is configured for fluid flow, such as, for example, arterial blood flow to remove blood from the subject. The first and second lumens may be configured for various forms of fluid flow in various directions and orientations, according to the requirements of a particular catheter application. The lumens are also configured to accommodate reversible flow such that lumen 26 removes blood and lumen 28 returns blood, as will be discussed and in accordance with the principles of the present disclosure.

Lumens 26, 28 may be uniformly dimensioned or include alternative dimensional cross sections within tubular body 22, such as, alternate geometrically configured portions, narrow and broad portions, converging surfaces, undulating surfaces, etc. according to the particular flow indications and/or flow rate requirements. It is contemplated venous lumen 26 and arterial lumen 28 may extend alternative lengths. It is further contemplated that tubular body 22 may include one or a plurality of lumens. It is envisioned that the first lumen may include the arterial lumen and the second lumen may include the venous lumen.

Venous lumen 26 and arterial lumen 28 are disposed in a substantially parallel orientation adjacent the distal end of tubular body 22. The distal end may extend various lengths and may include portions of tubular body 22 that are in a non-parallel orientation. It is also contemplated that venous lumen 26 and arterial lumen 28 may be spaced apart.

Figure 3:
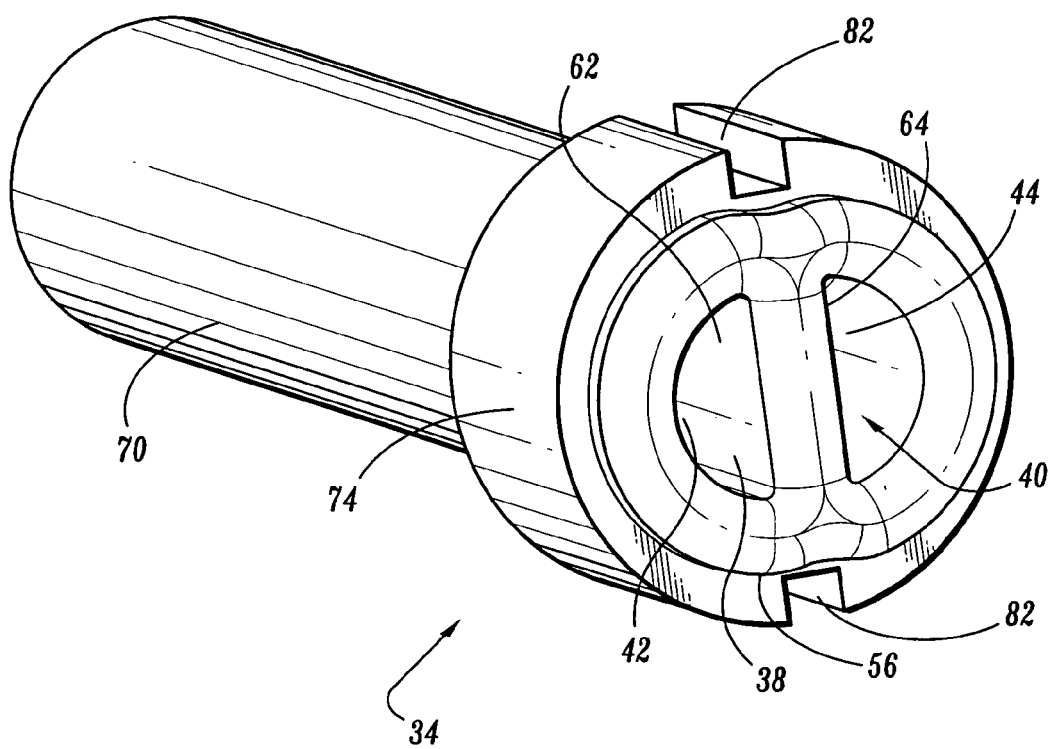
FIG. 3 is a perspective view of a portion of a hub and a valve of the catheter shown in FIG. 1.

Proximal end 24 includes an integral hub 32 having a valve 34. Valve 34 is configured to engage a proximal face 36 of tubular body 22. Valve 34 includes a first port 38 and a second port 40, as shown in FIG. 3, that are configured to align with lumens 26, 28 for establishing fluid communication between lumens 26, 28 and ports 38, 40, as will be discussed. Port 38 is aligned with a first conduit 42 of hub 32 and port 40 is a aligned with a second conduit 44 of hub 32. First conduit 42 is connected via coupling 46 to a venous blood line 48 and second conduit 44 is connected via coupling 50 to arterial blood line 52. Venous blood line 48 and arterial blood line 52 are attachable components of a medical apparatus, such as, for example, a hemodialysis device 54. Lines 48, 52 may be disposable. Hub 32 and valve 34 are integral with body 22 of catheter 20 in an advantageous configuration that eliminates the need for attaching additional accessories, such as, for example, tubes, clamps and extensions, in a hemodialysis treatment(s). This structure facilitates reusability of catheter 20 for multiple treatments, which is convenient and reduces associated cost.

Ports 38, 40 include a raised surface 56 that is configured to engage the openings of lumens 26, 28 adjacent proximal face 36. Raised surface 56 is disposed within a recess 58 of proximal end 24 that is formed by a lip 60. Raised surface 56 abuts proximal face 36 to form a fluid tight seal therebetween and establish fluid communication between lumens 26, 28 and ports 38, 40.

Raised surface 56 is flexible to provide conformity with proximal face 36 and facilitate seal formation. The flexibility of raised surface 56 also facilitates rotation of ports 38, 40 for reversing fluid flow within lumens 26, 28 to provide bi-directional flow in accordance with the principles of the present disclosure. For example, by manipulating catheter 20 and rotating hub 32, as will be discussed, ports 38, 40 are rotated into alignment with lumens 26, 28, respectively, into a first position. In the first position, lumen 26 is aligned with first conduit 42 to return treated blood to the subject from hemodialysis device 54 via venous blood line 48. Lumen 28 is aligned with second conduit 44 to remove blood from the subject to hemodialysis device 54 via arterial blood line 52. To reverse blood flow in the lumen, hub 32 is manipulated, in a clockwise or counterclockwise direction, to rotate port 38 out of alignment with lumen 26 and port 40 out of alignment with lumen 28. Ports 38, 40 maintain alignment with conduits 42, 44 through rotation of hub 32.

Ports 38, 40 are rotated into a second position such that port 38 is aligned with lumen 28 and port 40 is aligned with lumen 26 to facilitate reversible flow in catheter 20. Raised surface 56 abuts proximal face 36 to establish fluid communication between ports 38, 40 and lumens 28, 26, respectively. In the second position, lumen 26 is aligned with second conduit 44 to remove blood from the subject to hemodialysis device 54 via arterial blood line 52. Lumen 28 is aligned with first conduit 42 to return treated blood to the subject from hemodialysis device 54 via venous blood line 48. From the first position and the second position, ports 38, 40 are rotatable to a third position such that ports 38, 40 are not aligned with lumens 26, 28 and fluid communication between conduits 42, 44 and lumens 26, 28 is prevented. Ports 38, 40 may be rotated in a clockwise or a counterclockwise orientation from either the first position or the second position. It is contemplated that valve 34 may include various positions during rotation, such as, for example, in the order of :on position, off, reverse-on, off. 30. It is envisioned that ports 38, 40 are rotatable to establish fluid communication between lumens 26, 28 and conduits 42, 44 such that fluid communication is substantially not interrupted.

Ports 38, 40 each have a substantially D-shaped or semicircular configuration. First conduit 42 includes an inner surface 62 having a substantially planar portion and a substantially arcuate portion. Second conduit 44 similarly includes an inner surface 64 having a planar portion and an arcuate portion. Conduits 42, 44 are elongated with hub 32 and inner surfaces 62, 64 are configured to facilitate fluid flow within hub 32. It is contemplated that conduits 42, 44 may have various configurations, such as, for example, cylindrical, rectangular, elliptical, polygomal, etc. For example, in an alternate embodiment as shown in FIG. 4, hub 32 includes a first conduit 142 and a second conduit 144 having substantially triangular cross-sections. The triangular cross-sections include arcuate legs 145 and are configured to align with lumens 126, 128 for establishing fluid communication.

Figure 7:
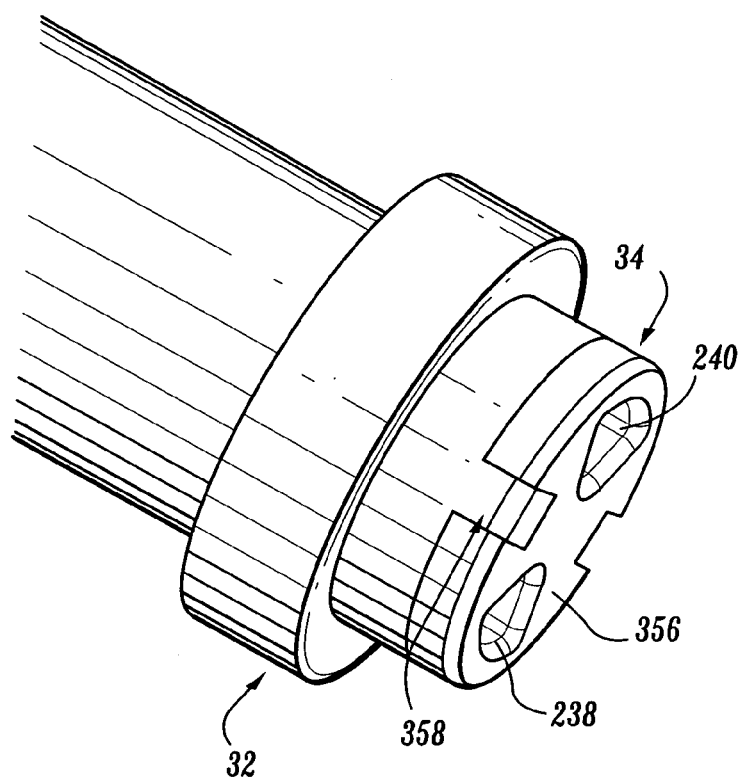
FIG. 7 is a perspective view of an alternate embodiment of the hub and the valve shown in FIG. 6.
Figure 6:
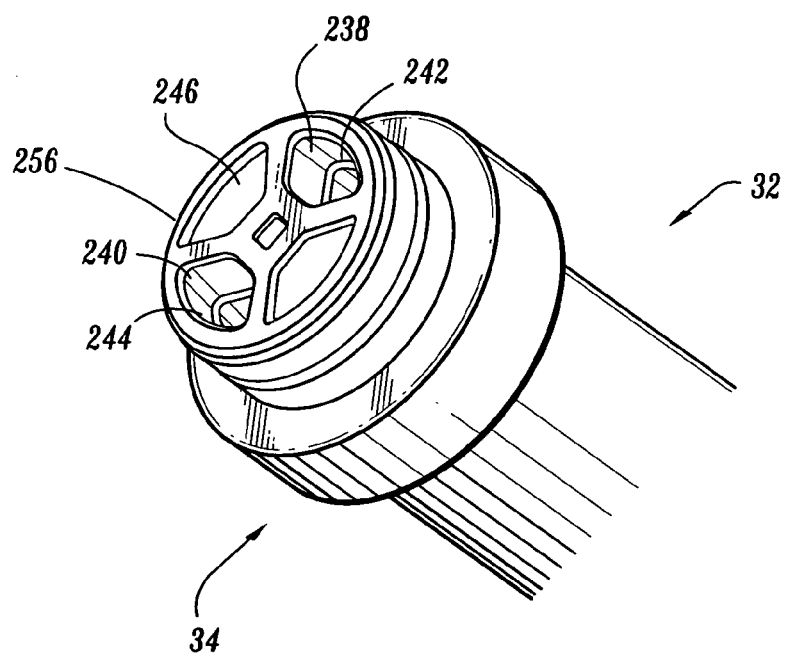
FIG. 6 is a perspective view of an alternate embodiment of the hub and the valve shown in FIG. 3.

In another alternate embodiment as shown in FIGS. 5 and 6, hub 32 includes a first conduit 242 and a second conduit 244 having sector configurations and separated by a central portion 246. Valve 34 includes a first port 238 and a second port 240 that are configured to align with lumens 226, 228 for establishing fluid communication. Ports 238, 240 include a raised surface 256 configured to engage the openings of lumens 226, 228 to establish fluid communication, similar to raised surface 56, described above. Alternatively, as shown in FIG. 7, ports 238, 240 include a planar face 356 configured to engage the openings of lumens 226, 228 to establish fluid communication between lumens 226, 228 and ports 238, 240. Hub 32 includes a lug 358 that is received by a cavity of valve 34 to facilitate rotation thereof.

Valve 34 is releasably lockable with body 22 to fix valve 34 in the first position and the second position. A locking member, such as, for example, sleeve 66 is connected with hub 32 and movable relative to body 22. Sleeve 66 releasably locks ports 38, 40 with proximal face 36 in the first position and the second position to maintain sealed fluid communication with lumens 26, 28. Sleeve 66 is biased, via spring 68, in the distal direction along catheter 20 to force ports 38, 40 into engagement with proximal face 36. It is envisioned that sleeve 66 may be biased alternatively by resilient bands, elastics, spring force pistons, etc. It is further envisioned that sleeve 66 may be biased in the proximal direction along catheter 20 or that biasing structure may be employed exterior to sleeve 66.

Spring 68 is coiled about a shaft 70 of hub 32 and has an end that is disposed with a proximal end 72 of sleeve 66. Spring 68 extends distally along shaft 70 to a flange 74. A distal end 76 of sleeve 66 is mounted about a proximal flange 78 of body 22. Thus, as spring 68 expands the ends of spring 68 engage proximal end 72 and flange 74. Engagement with proximal end 72 forces distal end 76 into engagement with flange 78. The spring force of spring 68 then results in expansion against flange 74 that drives ports 38, 40 into sealing engagement with proximal face 36 to maintain sealed fluid connection with lumens 26, 28.

Sleeve 66 includes radially inward projecting tabs 80 configured for disposal within a grooved slot 82 of flange 74. Grooved slot 82 facilitates axial movement of sleeve 66 via tabs 80. Grooved slot 82 restricts movement of sleeve 66 relative to flange 74. This restricted movement facilitates rotation of ports 38, 40, as will be discussed.

Distal end 76 includes projections 84 configured for disposal within cavities 86 of proximal flange 78. Projections 84 are fixed within cavities 86 to releasably lock sleeve 66 in the first position and the second position. Projections 84 are releasable from cavities 86 upon manipulation of sleeve 66, as will be discussed. Sleeve 66 is fabricated from a substantially transparent material, however, other materials are also contemplated.

In use, a catheter 20, similar to that described, is assembled, properly sterilized and otherwise prepared for storage, shipment and use in a hemodialysis procedure. A practitioner (not shown) manipulates the distal end of tubular body 22 for insertion within a body cavity of a subject (not shown). The distal end is inserted within a blood vessel of the subject. Catheter 20 is employed for administration of fluids that includes the simultaneous introduction of venous blood flow and withdrawal of arterial blood flow.

For example, catheter 20 may be inserted via subcutaneous tunneling or reverse tunneling as is known in the art. See, for example, U.S. Pat. Nos. 4,832,687 and 5,944,732, which are hereby incorporated herein in their entirety. The method of insertion may or may not use a subcutaneous tunneling device. Tubular body 22 may include a tunneling device having a centrally located dilator portion (not shown) and a generally pointed trocar (not shown). Body 22 also includes an insert (not shown) having two tines for insertion into lumens 26, 28 adjacent the distal end thereof. It should be understood that alternative devices, which are capable of performing the steps of the method may also be used.

The trocar end of the tunneling device is inserted through a first location on a cutaneous surface of a subject and moved through subcutaneous tissue to partially form a subcutaneous tunnel. For example, the trocar end is inserted through the cutaneous surface of the first location at or near the chest of the subject and then used for tunneling through the location up and out of another incision in the neck of the subject. As the tunneling device is tunneling through subcutaneous skin, the point of the trocar will pierce through a second location on the cutaneous surface to form the second end of the tunnel at or near the neck of the subject. The tunnel formed is generally from about 2 to 5 inches in length. The distal end of catheter 20 is then pulled through the tunnel leaving the hub portion of catheter 20 at or near the appropriate chest position. Once out through the neck incision, the distal end of catheter 20 is then inserted into the jugular at the neck and routed to the heart.

Preferably, an incision is created at the first location prior to inserting the trocar end of the tunneling device, such as by using a scalpel to cut through the cutaneous surface. However, it is within the scope of the present disclosure to directly pierce through the first location on the cutaneous surface with the trocar point of the tunneling device.

The tunneling device is withdrawn from the dilated tunnel section of the subcutaneous tunnel through the second end of the tunnel pulling through attached catheter 20. A completed subcutaneous tunnel and dilated section are formed. The practitioner uses the trocar for pulling proximal end 24 of body 22 through the tunnel.

The subcutaneous tunnel created by the subcutaneous tunneling device and the method of the present disclosure has a variety of applications. A particular use for a subcutaneous tunnel formed by the tunneling device and the method of the present disclosure is for trimming catheter 20 to a customizable length after catheter 20 has been positioned within a subject. The trimming process ensures that catheter 20 is of appropriate length as determined by the practitioner. The trimming process involves cutting catheter 20 at a certain point outside the body of the subject and fastening the cut end to hub 32. The connection point of trimmed catheter 20 and proximal end 24 can occur at hub 32 or distally thereof, as is well known in the art of catheter repair. Also contemplated is stabilizing proximal end 24 after the distal end has been positioned into the vein, another subcutaneous vessel, a body cavity or other area for removal or return of fluids of the subject. Furthermore, an alternate use of the tunnel is for securing catheter 20 with proximal end 24, which alternatively includes a stabilizing cuff (not shown), typically a fabric tissue ingrowths cuff, wrapped around its exterior to the skin of the subject. Alternative methods and accompanying structure may be employed with catheter 20 for insertion within a body cavity of a subject, according to the requirements of a particular application.

As shown in FIG. 1, catheter 20 is inserted with the blood vessel of the subject in a first position of valve 34 such that blood is withdrawn, via arterial blood flow in lumen 28, from the blood vessel for treatment by hemodialysis device 54 and the treated blood is introduced back into the blood vessel, via venous blood flow in lumen 26. Port 38 is aligned with lumen 26 and port 40 is aligned with lumen 28 to establish fluid communication with conduits 42, 44, as discussed.

To facilitate bi-directional fluid flow and reverse fluid direction of lumens 26, 28, sleeve 66 and hub 32 are manipulated in accordance with the principles of the present disclosure to resolve occlusion of lumens 26, 28 by, for example, removing, blowing, etc., clotting, fibrin sheath formation, etc. that may have formed during use of catheter 20. It is contemplated that hub 32 may be manipulated to reverse fluid flow for preventing occlusion of lumens 26, 28. For example, the efficient reversal of fluid flow in accordance with the present disclosure and achieved via the components of catheter 20 described herein, prevents occlusion of lumens 26, 28 by periodically reversing the direction of flow in catheter 20. This advantageous feature enhances dialysis delivery to the subject and prevents flow reduction by avoiding blood component buildup.

Figure 8:
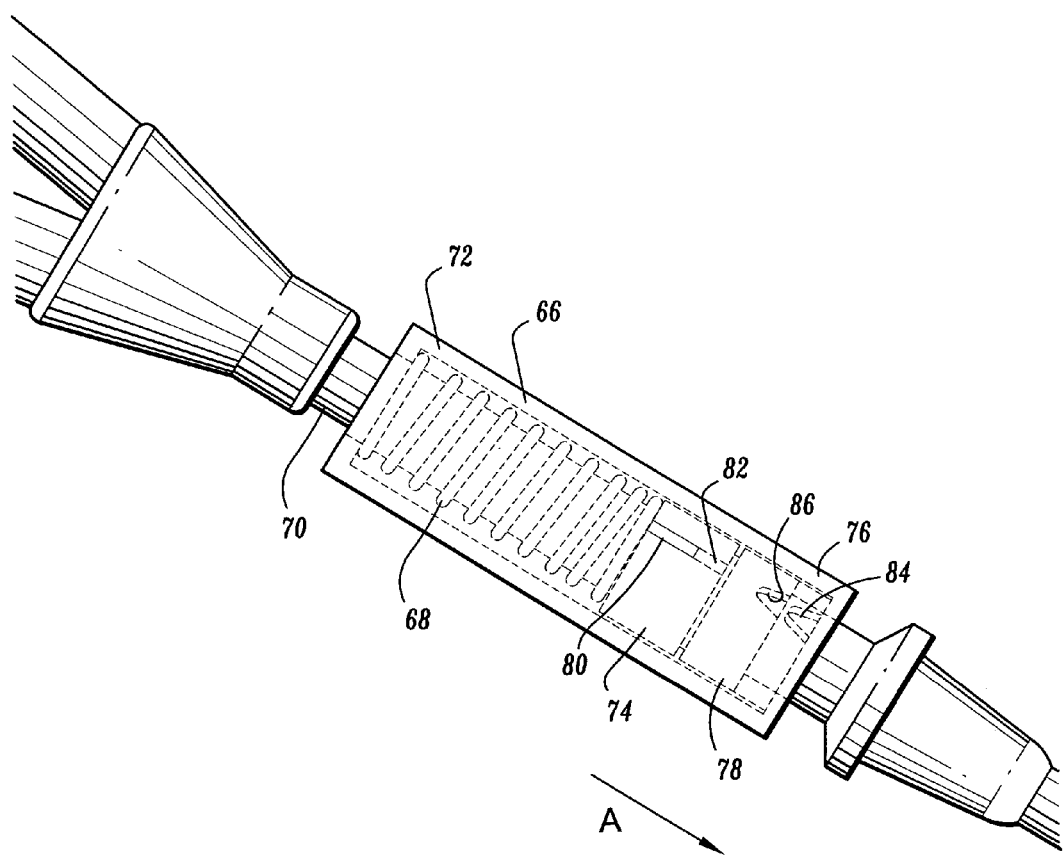
FIG. 8 is a perspective view of the catheter shown in FIG. 1 being released from a first position.

From the first position, if it is desirable to reverse fluid flow of lumens 26, 28, sleeve 66 is manipulated axially in a distal direction, as shown by arrow A in FIG. 8. Spring 68 contracts to increase its resultant spring force. Projections 84 are released from cavities 86 and tab 80 freely slides axially within groove 82.

Figure 9:
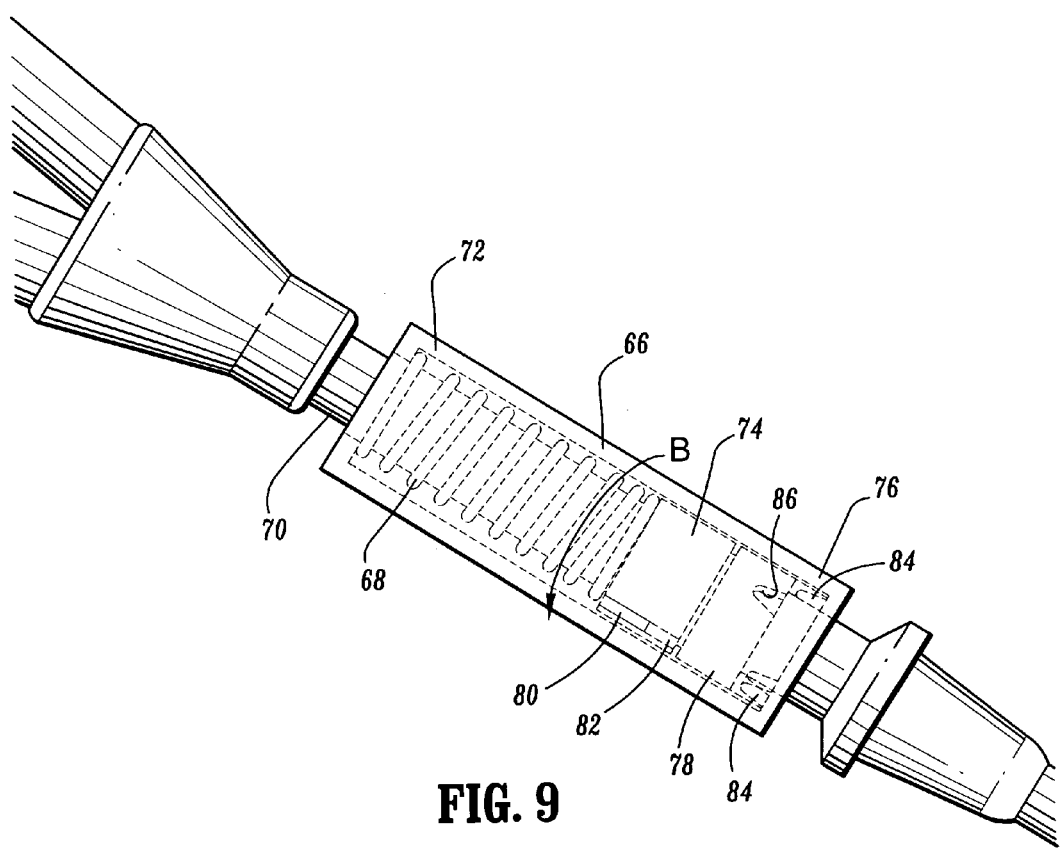
FIG. 9 is a perspective view of the catheter shown in FIG. 1 in an alternate position.
Figure 10:
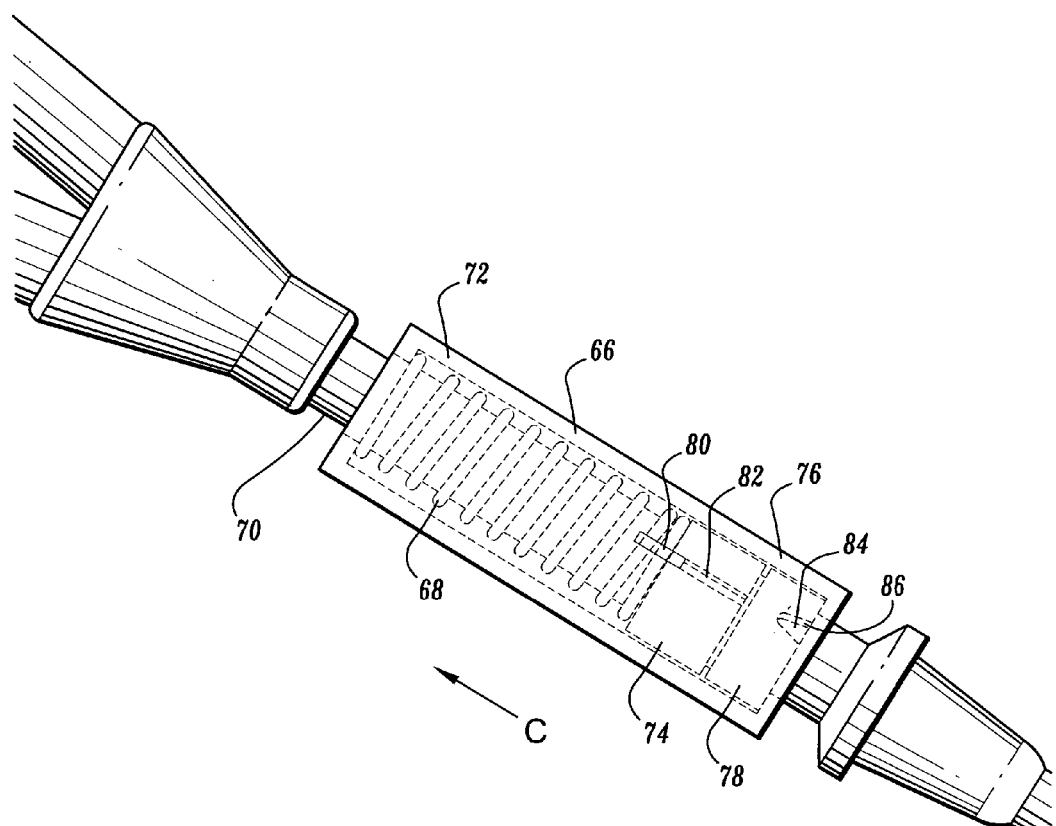
FIG. 10 is a perspective view of the catheter shown in FIG. 1 in a second position.

Sleeve 66 is rotated in a clockwise or counterclockwise direction, about a longitudinal axis defined by body 22, and projections 84 rotate about proximal flange 78. Tab 80 engages the surface of groove 82 causing flange 74 to correspondingly rotate, as shown by arrow B in FIG. 9. In turn, ports 38, 40 are rotated out of sealed alignment with lumens 26, 28. Rotation of sleeve 66 is continued through an angle of 180° to a second position such that port 38 is aligned with lumen 28 and port 40 is aligned with lumen 26 to establish sealed fluid communication with conduits 42, 44, as shown in FIG. 10. In the second position of valve 34, blood is withdrawn via arterial blood flow in lumen 26, from the blood vessel for treatment by hemodialysis device 54 and the treated blood is introduced back into the blood vessel, via venous blood flow in lumen 26.

Projections 84 are disposed within cavities 86 and sleeve 66 slides axially in a proximal direction, as shown by arrow C in FIG. 10, as spring 68 expands. Projections 84 are fixed in cavities 86 as facilitated by the bias of spring 68 to releasably lock sleeve 66 and valve 34, in the second position. From the first position and the second position, sleeve 66 may be manipulated distally to release projection 84 from cavities 86 to dispose valve 34 in a third position. In the third position, ports 38, 40 are rotated about the longitudinal axis of body 22, 90° for example, out of alignment with lumens 26, 28 to prevent fluid communication with conduits 42, 44. In the third position, hemodialysis treatment may be suspended for a desired period of time or terminated.

Figure 11:
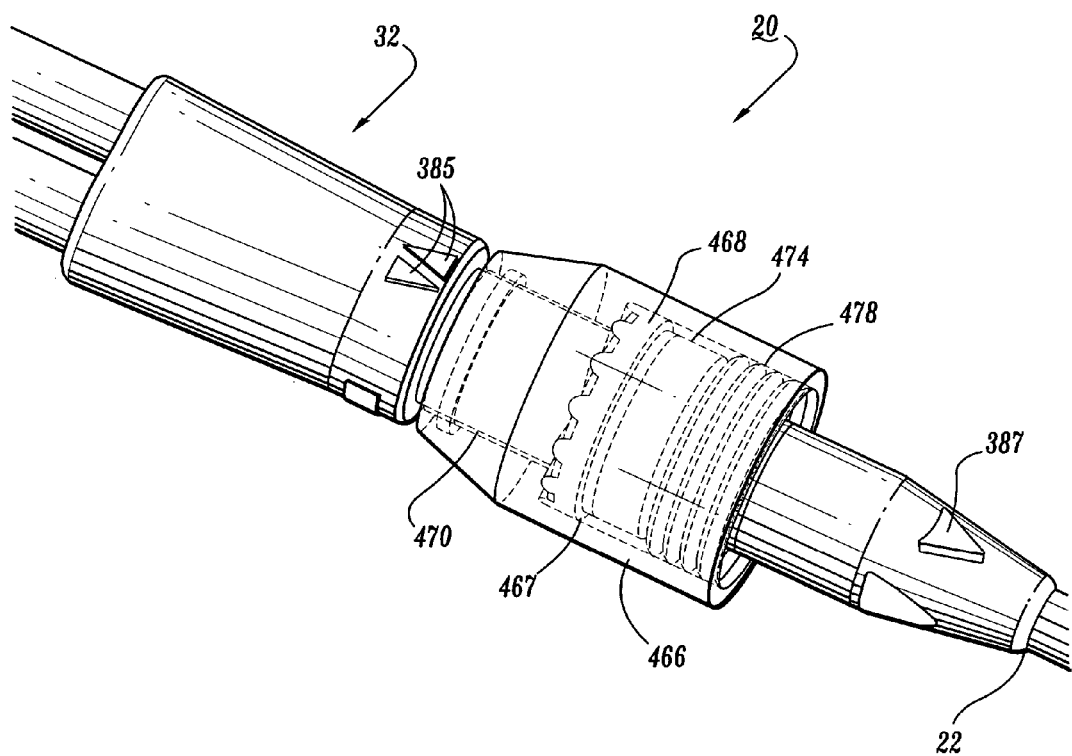
FIG. 11 is a perspective view of an alternate embodiment of the catheter shown in FIG. 1.
Figure 12:
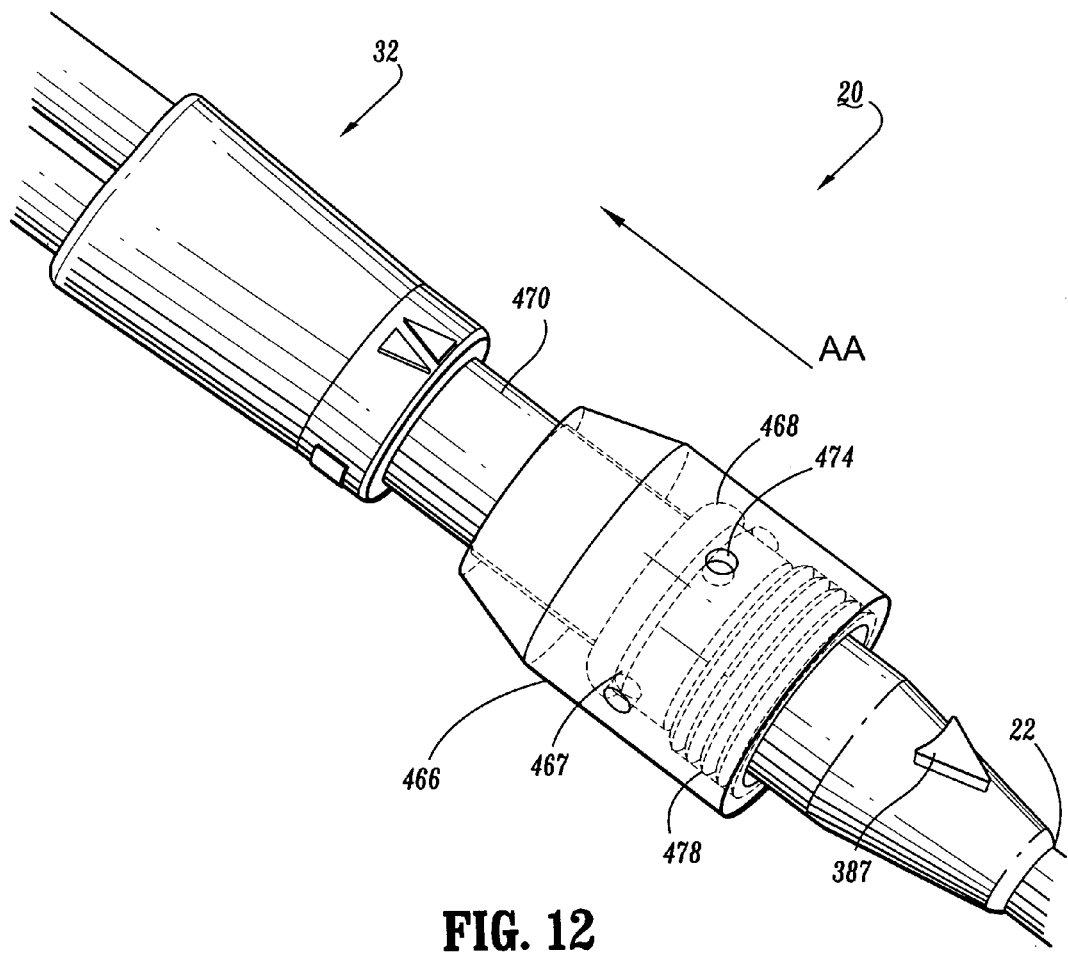
FIG. 12 is an alternate perspective view of the catheter shown in FIG. 11.

Referring to FIGS. 11 and 12, an alternate embodiment of catheter 20, similar to that described, is shown that includes a locking member, such as, for example, a sleeve 466, similar to sleeve 66. Sleeve 466 is substantially transparent, connected with hub 32 and mounted with a threaded flange 478 of body 22. Sleeve 466 releasably locks ports 38, 40 with proximal face 36 in the first position and the second position, described above, to maintain sealed fluid communication with lumens 26, 28. Sleeve 466 is biased, via a spring washer 468, to force ports 38, 40 into engagement with proximal face 36.

Spring washer 468 is mounted with a shaft 470 of hub 32 and extends distally to a flange 474. Engagement of spring washer 468 with flange 474 drives ports 38, 40 into sealing engagement with proximal face 36 to maintain sealed fluid connection with lumens 26, 28. Ports 38, 40 have an elastomeric face that engages proximal face 36 to facilitate sealing engagement. A slip washer 467 is disposed between spring washer 468 and flange 474 to facilitate independent movement of shaft 470 and flange 474 without excess friction.

Spring washer 468 maintains ports 38, 40 in sealed fluid communication with lumens 26, 28 under a load across a range of positional distance along the longitudinal axis defined by body 22. This configuration advantageously facilitates continuous engagement of the elastomeric face of ports 38, 40 and proximal face 36.

To facilitate bi-directional fluid flow and reverse fluid direction of lumens 26, 28, sleeve 466 and hub 32 are manipulated in accordance with the principles of the present disclosure. In the first position as shown in FIG. 11, fluid is withdrawn via lumen 28 for treatment and the treated fluid is introduced back via lumen 26, as discussed. Port 38 is aligned with lumen 26 and port 40 is aligned with lumen 28 to establish fluid communication with conduits 42, 44, respectively, as indicated by visual indicia 385, 387. Visual indicia 385, formed with hub 32, include raised surfaces configured as arrows. These arrows indicate fluid flow direction in conduits 42, 44. As shown, the arrow corresponding to conduit 42 illustrates distal fluid flow, corresponding to fluid return by lumen 26. The arrow corresponding to conduit 44 illustrates proximal fluid flow, corresponding to removal by lumen 28. Visual indicia 387, formed with body 22, includes raised surfaces configured as arrows to similarly demonstrate fluid flow direction in lumens 26, 28. Visual indicia 387 are disposed on opposing sides of body 22. Other configurations of the visual indicia are also contemplated.

From the first position, fluid flow of lumens 26, 28, is reversed by manipulating sleeve 466 and hub 32 axially in a proximal direction, as shown by arrow AA in FIG. 12.

Flange 474 retracts slightly to relieve a portion of the load that drives ports 38, 40 into sealing engagement with proximal face 36, while maintaining continuous engagement of the elastomeric face of ports 38, 40 and proximal face 36.

Sleeve 466 is rotated in a clockwise or counterclockwise direction, about a longitudinal axis defined by body 22, as facilitated by slip washer 467. In turn, ports 38, 40 are rotated out of sealed alignment with lumens 26, 28. Rotation of sleeve 466 is continued through an angle of 180° to a second position such that port 38 is aligned with lumen 28 and port 40 is aligned with lumen 26 to establish sealed fluid communication with conduits 42, 44. In the second position of valve 34, blood is withdrawn via arterial blood flow in lumen 26, from the blood vessel for treatment and the treated blood is introduced back into the blood vessel, via venous blood flow in lumen 28. Visual indicia 385, 387 correspondingly indicate fluid flow direction of conduits 42, 44 and lumens 26, 28.

Figure 13:
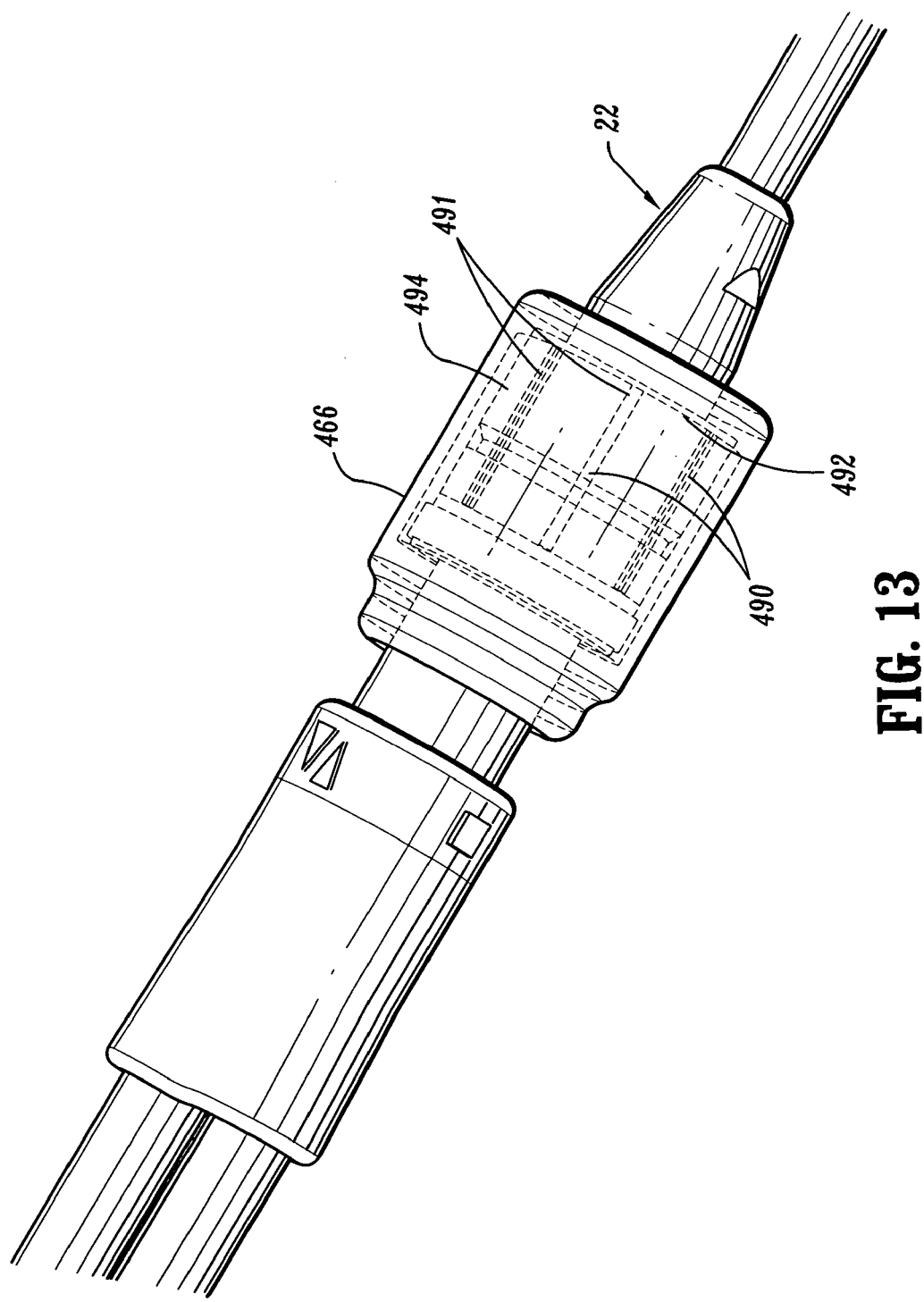
FIG. 13 is a perspective view of an alternate embodiment of the catheter shown in FIG. 11.
Figure 14:
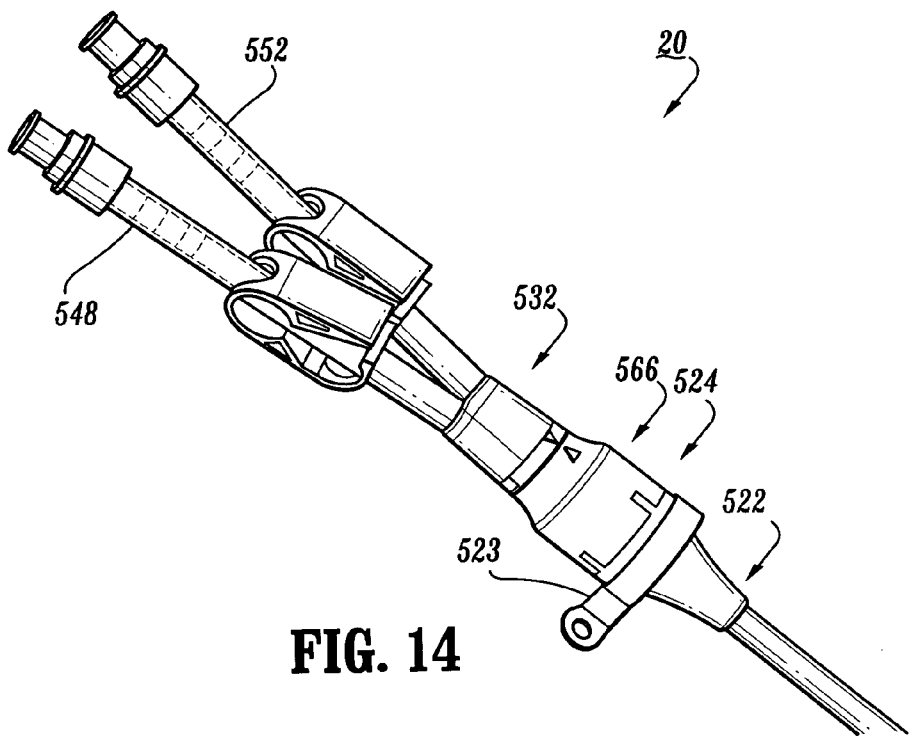
FIG. 14 is a perspective view of another alternate embodiment of the catheter shown in FIG. 1.
Figure 15:
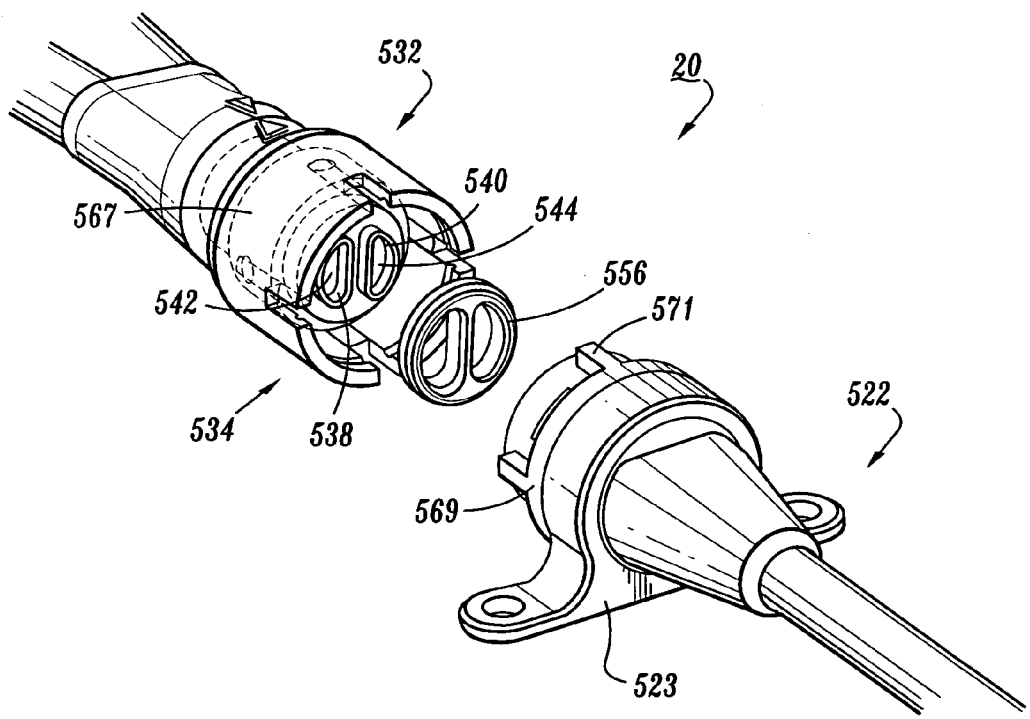
FIG. 15 is a cutaway perspective view, with parts separated, of the catheter shown in FIG. 14.
Figure 16:
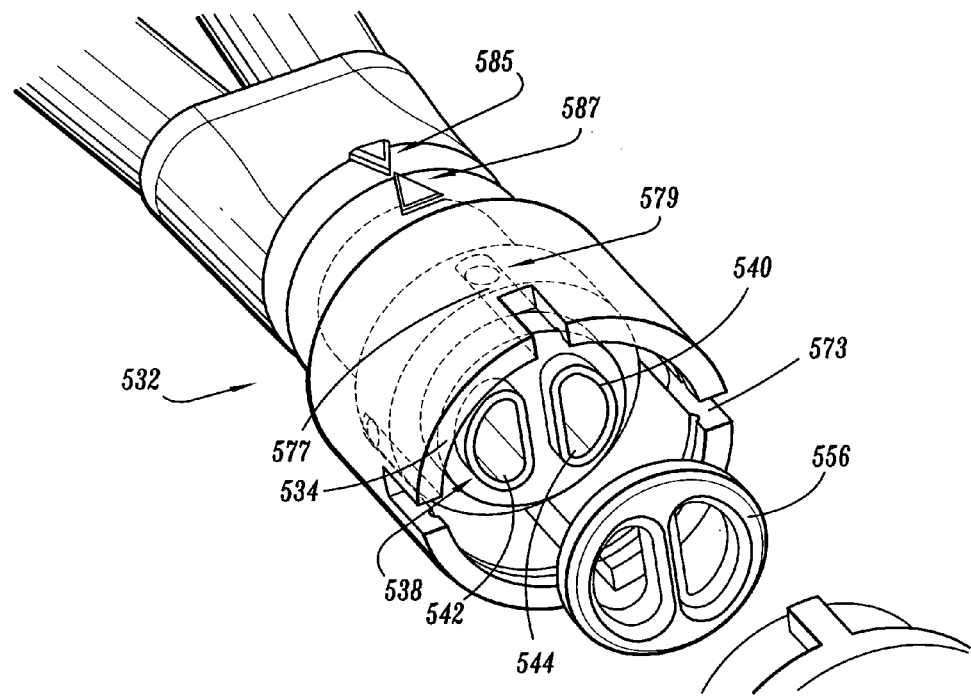
FIG. 16 is a cutaway perspective view, with parts separated, of the catheter shown in FIG. 14.
Figure 17:
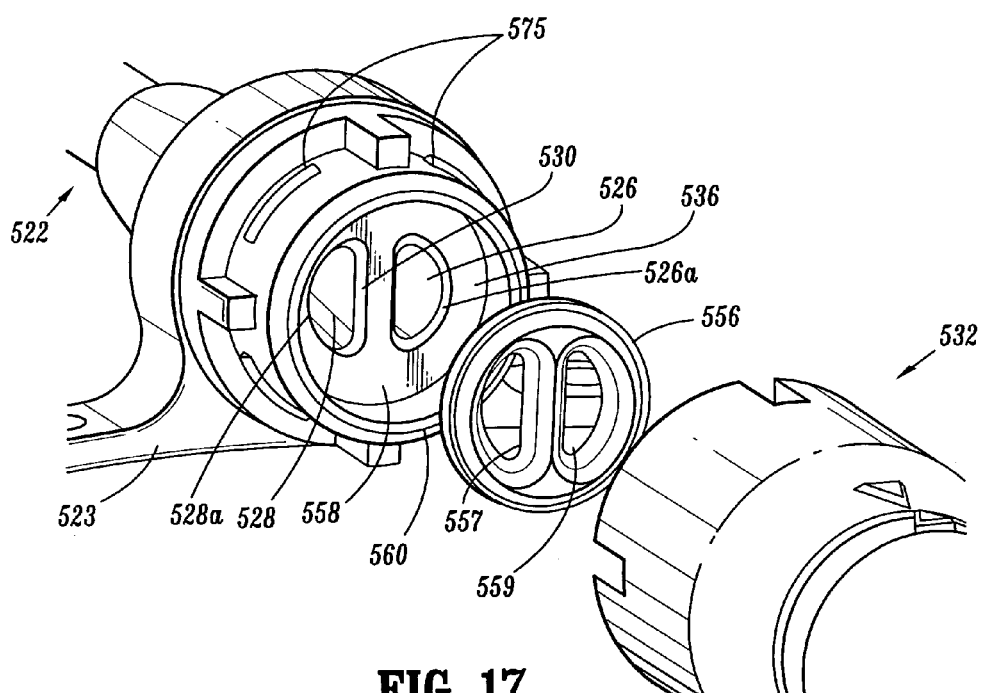
FIG. 17 is a cutaway perspective view, with parts separated, of the catheter shown in FIG. 14.

Referring to FIG. 13, an alternate embodiment of sleeve 466, similar to that shown in FIGS. 11 and 12, includes tabs 490 formed on an inner surface of sleeve 466. Tabs 490 extend axially, relative to the longitudinal axis of body 22, along the inner surface and include inner projections 491 disposed at a distal end of tabs 490. Inner projections 491 are configured for disposal within a coupling collar 492 of a flange 494 of body 22. Coupling collar 492 includes a groove defined about the circumference of flange 494. Tabs 490 are disposed about the inner circumference of sleeve 466 such that inner projections 491 snap into coupling collar 492 to facilitate mounting of sleeve 466 with body 22.

Tabs 490 facilitate flexing or spreading of sleeve 466 during assembly of the components of catheter 20. Upon outward flexing of sleeve 466, the components of catheter 20 are forced into sleeve 466. Upon assembly, tabs 490 flex back to their original unstressed geometry. This configuration advantageously couples the components so that the sealing surfaces are a set distance apart.

Referring to FIGS. 14–18, another alternate embodiment of catheter 20, similar to that described, is shown that includes a tubular body 522 having a proximal end 524 and a distal end (not shown). Tubular body 522 includes a stabilizer 523 disposed thereabout for mounting to a surface.

Tubular body 522 defines a venous lumen 526 and an arterial lumen 528 with a septum 530 disposed therebetween. Proximal end 524 includes an integral hub 532 having a valve 534. Valve 534 is configured to engage a proximal face 536 of tubular body 522. Valve 534 includes a first port 538 and a second port 540, that are configured to align with lumens 526, 528 for establishing fluid communication between lumens 526, 528 and ports 538, 540. Port 538 is aligned with a first conduit 542 of hub 532 and port 540 is a aligned with a second conduit 544 of hub 532. First conduit 542 is connected to a venous blood line 548 and second conduit 544 is connected to an arterial blood line 552. Venous blood line 548 and arterial blood line 552 are components of a medical apparatus, such as, for example, a hemodialysis device. Hub 532 and valve 534 are integral with body 522 of catheter 20 in an advantageous configuration that eliminates the need for attaching additional accessories, such as, for example, tubes, clamps and extensions, in a hemodialysis treatment(s). This structure facilitates reusability of catheter 20 for multiple treatments, which is convenient and reduces associated cost.

Valve 534 includes a elastomeric washer 556 that is configured for disposal between ports 538, 540 and proximal face 536 to engage the openings of lumens 526, 528. Elastomeric washer 556 defines openings 557 and 559 that mount about raised portions of ports 538, 540. Openings 557, 559 are non-circular and reduce the size and surface area associated with washer 556. The edges of openings 557, 559 are rounded to facilitate a robust seal and ease of relative movement during rotation of the ports to desired positions. This advantageous configuration reduces the potential for contamination, reduces the potential for harboring microorganisms and reduces friction on the surfaces of washer 556. The reduced surface area also requires less force for compression of the components of body 522, which reduces stress and improves integrity of the components. These features contribute to the ability to reuse catheter 20 for multiple treatments.

It is contemplated that washer 556 may have a lubricious compound impregnated therewith to prevent damage during repeated use over multiple treatments. It is envisioned that washer 556 may alternatively include circular openings. It is contemplated that washer 556 may include one or a plurality of openings. It is further contemplated that the openings of washer 556 may be alternately configured, for example, one opening having a first configuration and a second opening having a second configuration.

The raised portions of ports 538, 540 extend into openings 557, 559 to facilitate rotation of elastomeric washer 556 and sealing therewith. Elastomeric washer 556 is disposed within a recess 558 of proximal end 524 that is formed by a lip 560. Elastomeric washer 556 abuts proximal face 536 and ports 538, 540 to form a fluid tight seal therebetween and establish fluid communication between lumens 526, 528 and ports 538, 540. Lumens 526, 528 include ridges 526a, 528a respectively, that engage corresponding portions of elastomeric washer 556 to facilitate rotation and sealing therewith.

Figure 18:
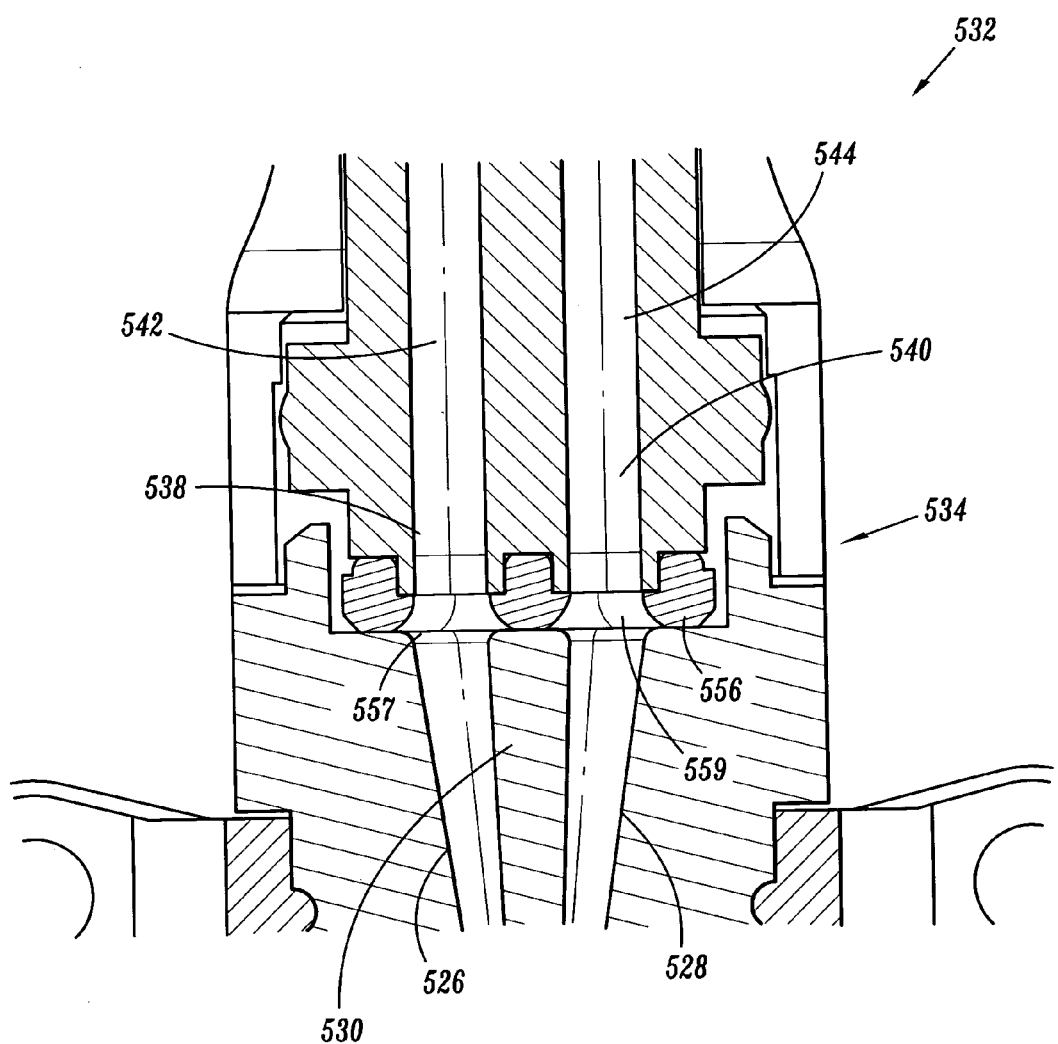
FIG. 18 is a cutaway cross-sectional view of the catheter shown in FIG. 14.
Figure 18A:
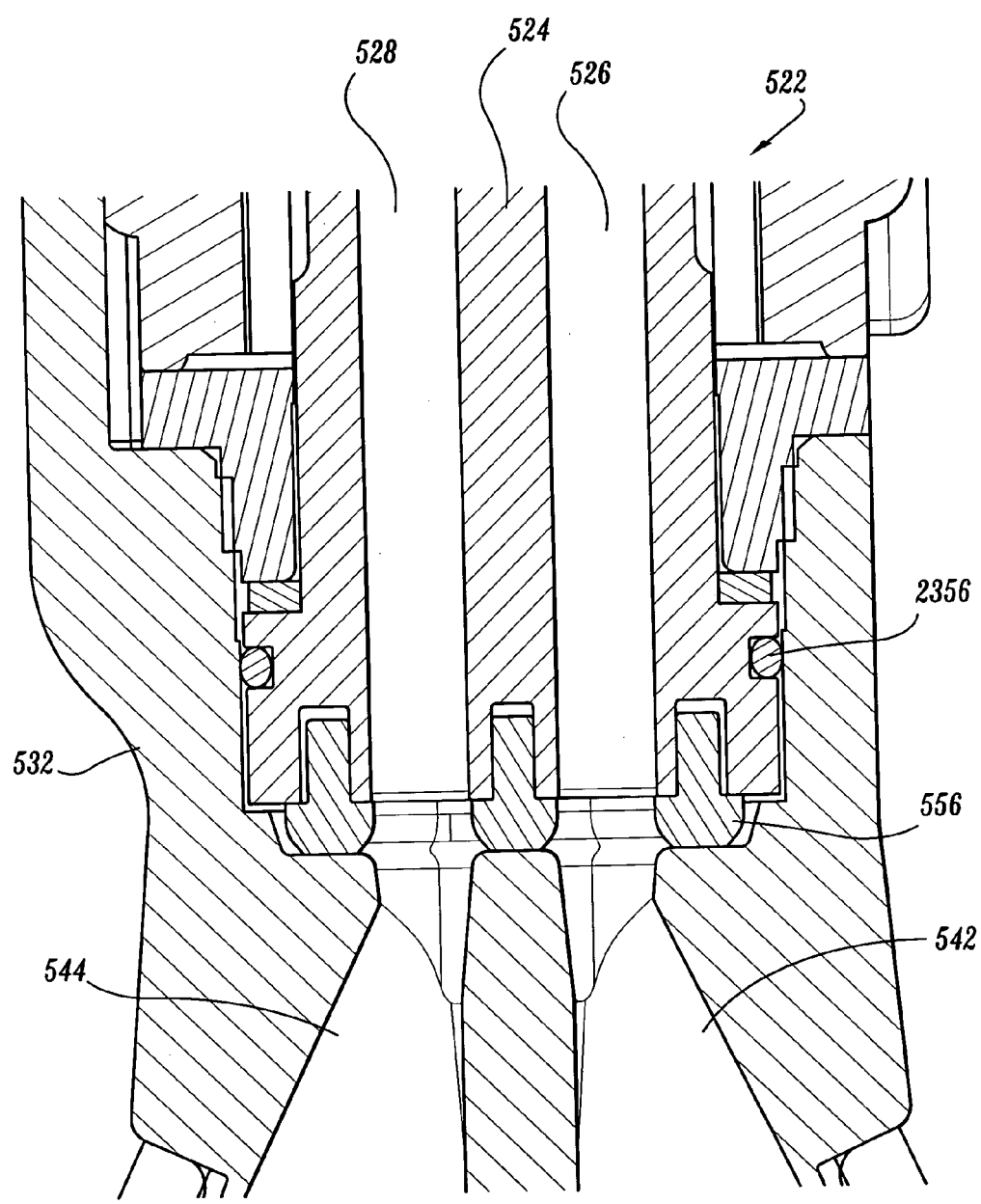
FIG. 18A is a cutaway cross-sectional view of an alternate embodiment of the catheter shown in FIG. 14.

Elastomeric washer 556 is flexible to provide conformity with ports 538, 540 and proximal face 536, and facilitate seal formation. The flexibility of elastomeric washer 556 also facilitates rotation of ports 538, 540 for reversing fluid flow within lumens 526, 528 to provide bi-directional flow in accordance with the principles of the present disclosure. For example, by manipulating catheter 20 and rotating hub 532, as discussed, ports 538, 540 are rotated into alignment with lumens 526, 528, respectively, into a first position, similar to that discussed above. In an alternate embodiment, as shown in FIG. 18A, catheter 20 includes a first seal, such as, for example, washer 556 and a second seal, such as, for example, O-ring member 2356. O-ring member 2356 is disposed between hub 532 and a portion of proximal end 524 of body 522, that supports lumens 526, 528, to facilitate sealing therebetween. It is contemplated that O-ring member 2356 is flexible to provide conformity, facilitate seal formation and relative rotation of the parts. It is further contemplated that O-ring member 2356 may be variously disposed along proximal end 524. It is envisioned that the second seal may comprise alternate structure such as, for example, a flat gasket, an extension from washer 556, or alternatively, catheter 20 may include a plurality of secondary seals.

In the first position, lumen 526 is aligned with first conduit 542 to return treated blood to the subject from the hemodialysis device via venous blood line 548. Lumen 528 is aligned with second conduit 544 to remove blood from the subject to the hemodialysis device via arterial blood line 552. To reverse blood flow in the lumen, hub 532 is manipulated, in a clockwise or counterclockwise direction, to rotate port 538 out of alignment with lumen 526 and port 540 out of alignment with lumen 528. Ports 538, 540 maintain alignment with conduits 542, 544 through rotation of hub 532. It is contemplated that hub 532 may be rotated in only one direction.

Ports 538, 540 are rotated into a second position such that port 538 is aligned with lumen 528 and port 540 is aligned with lumen 526 to facilitate reversible flow in catheter 20. Elastomeric washer 556 abuts proximal face 536 to establish fluid communication between ports 538, 540 and lumens 528, 526, respectively. In the second position, lumen 526 is aligned with second conduit 544 to remove blood from the subject to the hemodialysis device via arterial blood line 552. Lumen 528 is aligned with first conduit 542 to return treated blood to the subject from the hemodialysis device via venous blood line 548. Ports 538, 540 may be rotated in a clockwise or a counterclockwise orientation from either the first position or the second position.

Valve 534 is releasably lockable with body 522 to fix valve 534 in the first position and the second position. A sleeve 566 includes a hub part 567 and a tube part 569 that are assembled to rotate valve 534. Hub part 567 interlocks with tube part 569 to maintain the components of catheter 20 in assembly. Tube part 569 includes posts 571 that are received by channels 573 of hub part 567 for assembly thereof. Tube part 569 also includes a snap collar 575 that facilitates assembly with hub part 567.

Hub part 567 is mounted to hub 532 and includes axial grooves 577. Axial grooves 577 mount onto detents 579 of hub 532. Detents 579 are formed equidistantly about the circumference of hub 532. Grooves 577 are mounted for engagement with detents 579 and rotation of hub part 567 relative to hub 532, to facilitate lock step indexing for manipulating valve 534 into various positions. For example, initially valve is in the first on position described. Hub part 567 is rotated 90 degrees, in a lock step manner, to an off position. Hub part 567 is then further rotated 90 degrees to the second position described, reversible on. Hub part 567 is then rotated another 90 degrees to another off position.

Sleeve 566 releasably locks valve 534 is a desired position to maintain sealed fluid communication with lumens 526, 528. Catheter 20 includes visual indicia 585, 587, similar to that described above, to indicate alignment of the selectable positions, or alternatively, to indicate fluid flow direction in conduits 542, 544 and lumens 526, 528. It is contemplated visual indicia 585, 587 may be represented with symbols, color, etc.

Figure 19:
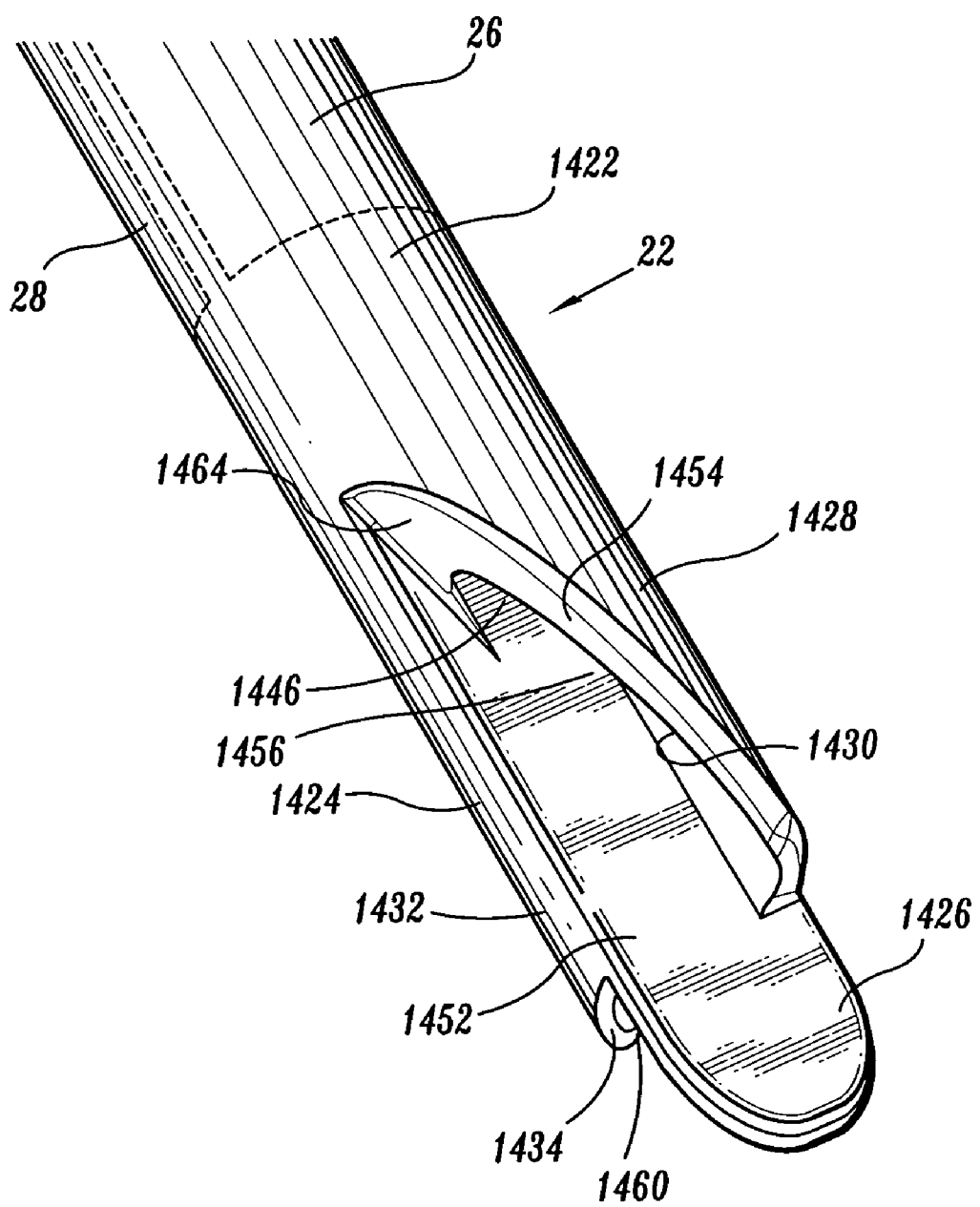
FIG. 19 is a cutaway perspective view of one particular embodiment of a distal end of the catheter shown in FIG. 1.
Figure 20:
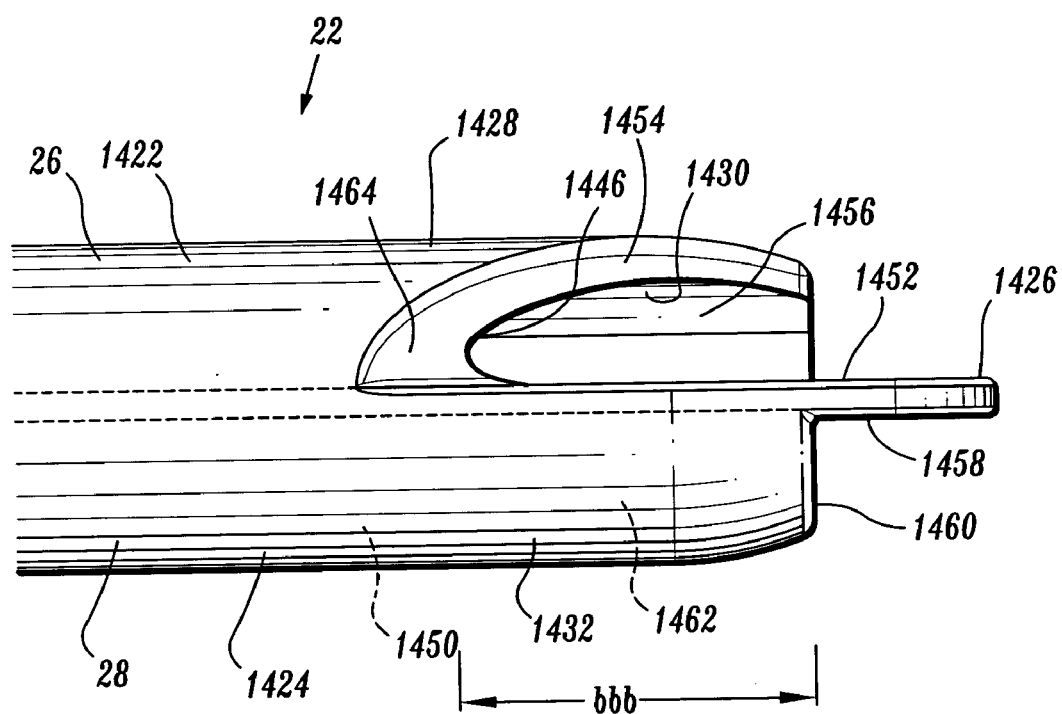
FIG. 20 is a side view of the distal end shown in FIG. 19.
Figure 21:
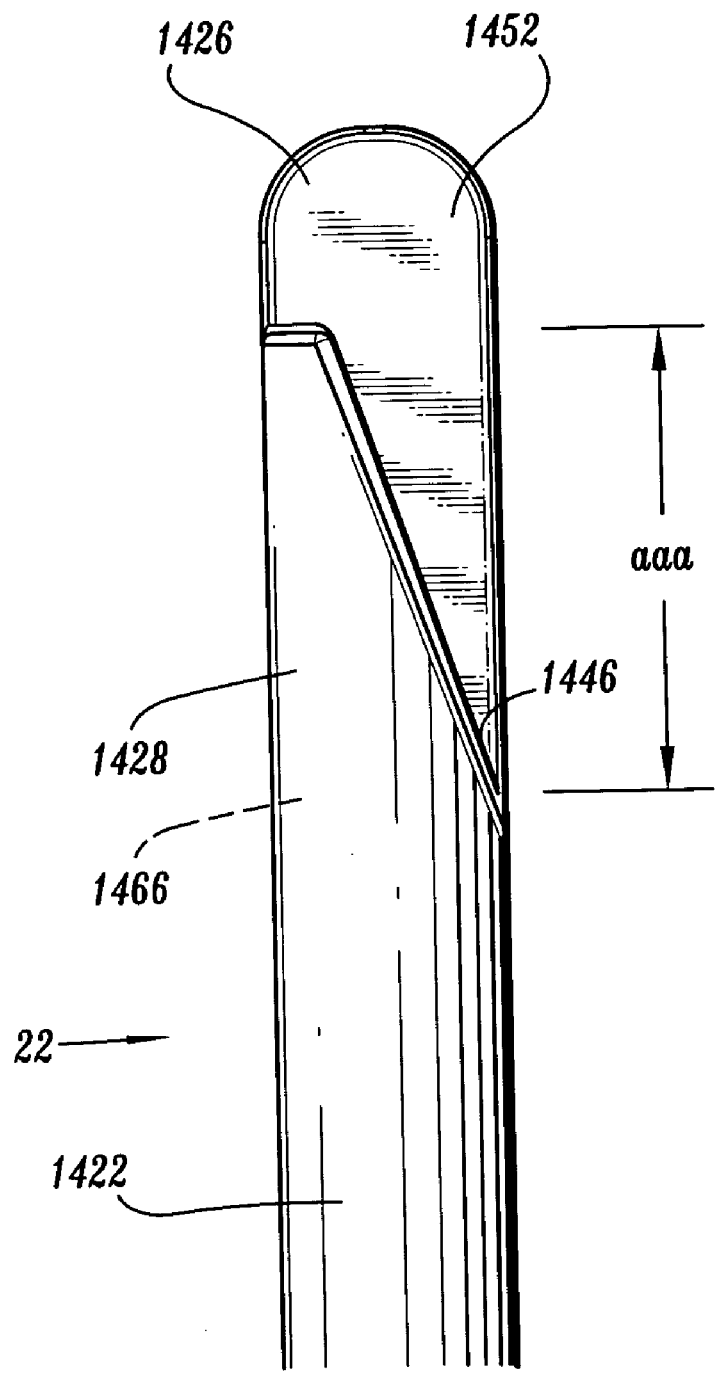
FIG. 21 is a top view of the distal end shown in FIG. 19.

Referring to FIGS. 19–21, an alternate embodiment of the distal end of catheter 20 is shown. The distal end of catheter 20 includes a first wall 1422 having a first wall extension 1428 that extends distally beyond venous lumen 26 and is spaced apart from a septum extension 1426. First wall extension 1428 defines a concave surface 1430 that faces septum extension 1426. Second wall 1424 includes a second wall extension 1432 that extends distally beyond arterial lumen 28 and is spaced apart from septum extension 1426. Second wall extension 1432 defines a concave surface 1434 that faces septum extension 1426.

First wall extension 1428 is circumferentially disposed about septum extension 1426 in a spiral configuration to facilitate fluid flow and prevent recirculation between lumens 26, 28. It is envisioned that first wall extension 1428 may include various spiral configurations, such as, for example, a more elongated spiral, a spiral having a more acute winding type design, helical, etc. First wall extension 1428 extends distally, a distance aaa, beyond opening 1446 of venous lumen 26 and opening 1450 (shown in phantom) of second lumen 28. It is contemplated that distance aaa may extend various lengths. Concave surface 1430 faces first planar surface 1452 of septum extension 1426 and is spaced apart therefrom.

Concave surface 1430 is bounded by a planar end surface 1454 of first wall extension 1428. End surface 1454 extends about the perimeter of concave surface 1430 in a spiral configuration, as described above, to facilitate fluid flow through venous lumen 26. Concave surface 1430 and first planar surface 1452 cooperate to define first cavity 1456. First cavity 1456 is further bounded by a proximal base 1464 of end surface 1454. Proximal base 1464 is formed with septum extension 1426 in an arcuate transition. Proximal base 1464 has an arcuate configuration and defines a proximal inlet/outlet portion for venous lumen 26. It is contemplated that during removal of fluids, venous lumen 26 has a greater fluid flow rate adjacent proximal base 1464.

Second wall extension 1432 is circumferentially disposed about septum extension 1426 in a spiral configuration to facilitate fluid flow and prevent recirculation between lumens 26, 28. It is envisioned that first wall extension 1432 may include various spiral configurations, such as, for example, a more elongated spiral, a spiral having a more acute winding type design, helical, etc. Second wall extension 1432 extends distally, a distance bbb, beyond opening 1450 (shown in phantom and similarly configured to opening 1446) and opening 1446. It is contemplated that distance bbb may extend various lengths. Concave surface 1434 faces second planar surface 1458, opposing first planar surface 1452, of septum extension 1426 and is spaced apart therefrom.

Concave surface 1434 is bounded by a planar end surface 1460 of second wall extension 1432. End surface 1460 (similarly configured to end surface 1454, although end surfaces 1454, 1460 may include alternative or distinct structure) extends about the perimeter of concave surface 1434 in a spiral configuration, as described above, to facilitate fluid flow through arterial lumen 28. Concave surface 1434 and second planar surface 1458 cooperate to define second cavity 1462 (shown in phantom), similar to that described above. Second cavity 1462 is further bounded by a proximal base 1466 of end surface 1460 (shown in phantom and similarly configured to base 1464, although bases 1464, 1466 may include alternative or distinct structure). Proximal base 1466 has an arcuate configuration and defines a proximal inlet/outlet portion for arterial lumen 28 during removal of fluids. It is contemplated that that during removal of fluids, arterial lumen 28 has a greater fluid flow rate adjacent proximal base 1466.

First wall extension 1428 and second wall extension 1432 are symmetrically disposed about septum extension 1426 such that first cavity 1456 and second cavity 1462 are symmetrical. First cavity 1456 and second cavity 1462 bound an equivalent space to facilitate inflow and outflow capability for each lumen.

The configuration of catheter 20 advantageously facilitates reversible flow between venous lumen 26 and arterial lumen 28 by alternating blood flow directions. As venous lumen 26 returns blood flow to the body vessel, blood flow is removed through arterial lumen 28. The blood flow is axially directed out of cavity 1456 past first wall extension 1430. It is envisioned that such axially directed blood flow washes away any blood clots disposed adjacent cavity 1456.

Arterial lumen 28 is provided with suction to remove fluids from the body vessel. The suction draws blood flow from various directions and orientations into opening 1450. Suction is greater adjacent proximal base 1466 due to its closer proximity to a suction source (not shown). Fluid flow is greater adjacent to proximal base 1466 and therefore, advantageously disposed proximal to the blood flow being expelled from cavity 1456 of venous lumen 26. This configuration minimizes recirculation between lumens 26, 28.

It is contemplated that blood clots, or other undesired particles, disposed adjacent cavity 1462 of arterial lumen 28 may be washed away by reversing blood flow direction of lumens 26, 28. Upon reversal of blood flow direction, blood flow is expelled from cavity 1462 and the axially directed blood flow washes away blood clots, similar to that described above.

Venous lumen 26 is removes fluids from the body vessel and into opening 1446. Second wall extension 1432 is symmetrical with first wall extension 1428, and therefore, similar to proximal base 1466, suction is greater adjacent proximal base 1464. Fluid flow is greater adjacent to proximal base 1464 and therefore, advantageously disposed proximal to the blood flow being expelled from cavity 1462. This configuration minimizes recirculation between lumens 26, 28.

Figure 22:
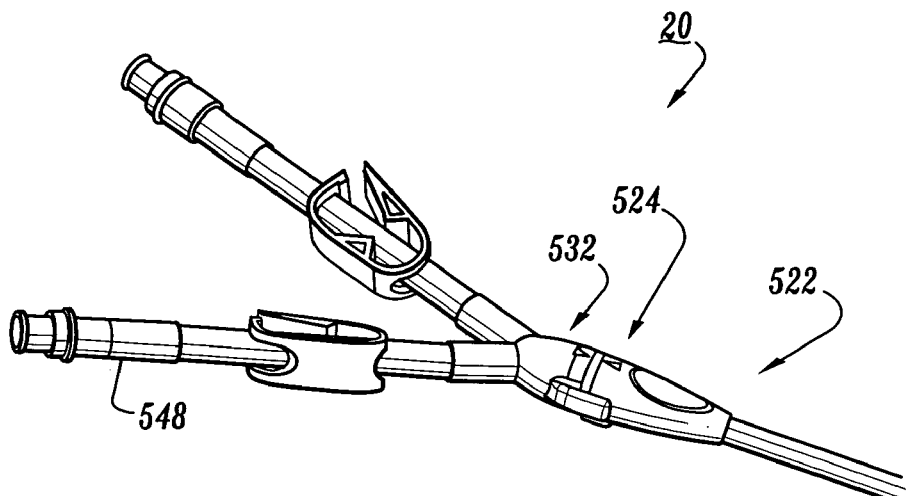
FIG. 22 is a perspective view of another alternate embodiment of the catheter shown in FIG. 1.
Figure 23:
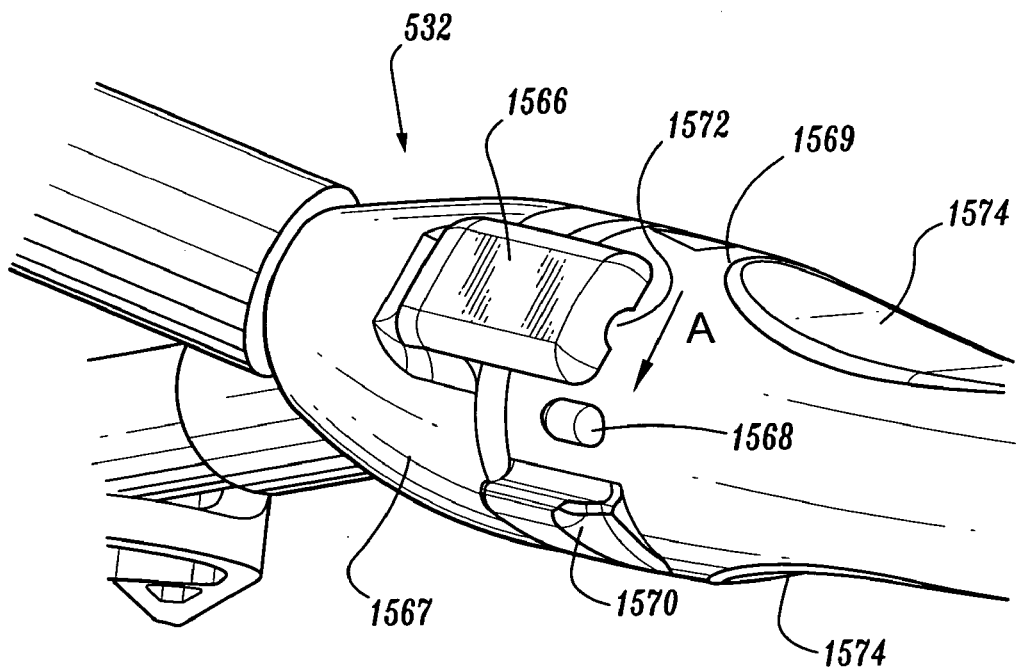
FIG. 23 is a cutaway perspective view of the catheter shown in FIG. 22.
Figure 24:
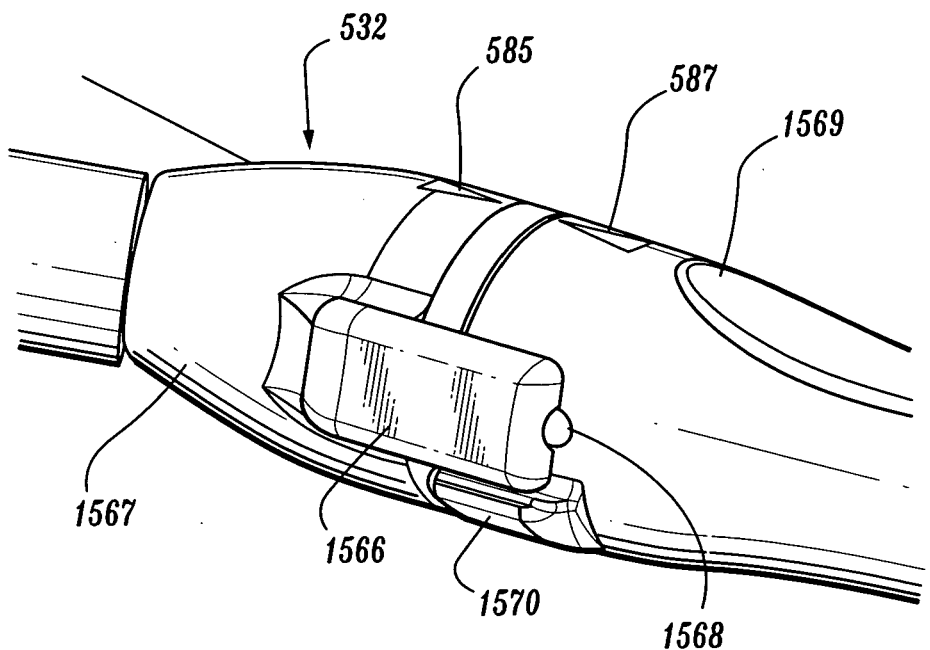
FIG. 24 is an alternate cutaway perspective view of the catheter shown in FIG. 22 in the locked position.

Referring to FIGS. 22–24, another alternate embodiment of catheter 20, similar to that described with regard to FIGS. 14–18, is shown that includes tubular body 522 having proximal end 524. Proximal end 524 includes integral hub 532 having valve 534 (not shown), similar to the components described above.

In the first position, the lumens are aligned with the conduits to return treated blood to the subject from the hemodialysis device via venous blood line 548, as described above. To reverse blood flow, hub 532 is manipulated, in a clockwise or counterclockwise direction, to rotate the ports into a second position, as described above. A hub part 1567 is mounted to hub 532 and a tube part 1569 is mounted with proximal end 524 to facilitate manipulation and connection of the components of catheter 20. Hub part 1567 and tube part 1569 are relatively rotatable to facilitate rotation of the ports between the first position and the second position. Depressions 1574 facilitate manipulation of tube part 1569. It is contemplated that parts 1567, 1569 may include alternate structure to facilitate manipulation thereof, such as, for example, arms, clips, motorized apparatus and applicable electronic devices.

An indexing mechanism of catheter 20 facilitates releasably locking of valve 534 with body 522 to fix valve 534 in the first position or the second position. The indexing mechanism includes an indexing tab 1566 that extends from hub part 1567 for relative movement about tube part 1569. In the first position or the second position, indexing tab 1566 is releasably engageable with detents 1568 of tube part 1569. Indexing tab 1566 has a cavity 1572 that receives detents 1568 to releasably lock hub part 1567 and tube part 1569 is a desired position.

Detents 1568 are diametrically disposed about the circumference of tube part 1569 to releasably lock indexing tab 1566 in the first position or the second position. Tab stops 1570 are diametrically disposed about the circumference of tube part 1569 and adjacent detents 1568 to prevent further rotation of indexing tab 1566 beyond the first position or the second position. For example, initially valve 534 is in the first on position described above. Hub part 1567 is rotated 90 degrees and indexed to an off position, as shown in FIG. 23. Hub part 1567 is then further rotated 90 degrees, as shown by arrow A in FIG. 23, to the second position described above, reversible on, as shown in FIG. 24. If desired, hub part 1567 can then be rotated another 90 degrees to another off position.

Indexing tab 1566 releasably engages detent 1568 and is prevented from further rotation by tab stop 1570 to releasably lock valve 534 is a desired position to maintain sealed fluid communication with lumens 526, 528 (not shown). The indexing mechanism of the present disclosure provides an advantageous locking feature that reduces bulk and surface area. This improves the ability to clean the surfaces of body 522 and facilitates reuse of catheter 20 for multiple treatments. Catheter 20 includes visual indicia 585, 587, similar to that described above, to indicate alignment of the selectable positions, or alternatively, to indicate fluid flow direction, as described.

Figure 25:
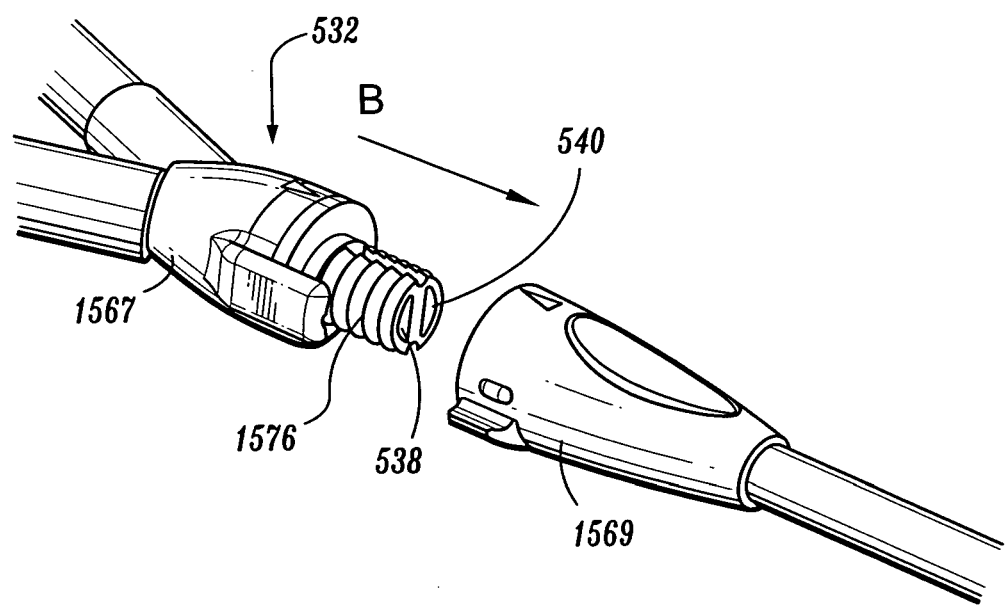
FIG. 25 is a cutaway perspective view of an alternate embodiment of the catheter shown in FIG. 22 with parts separated.
Figure 26:
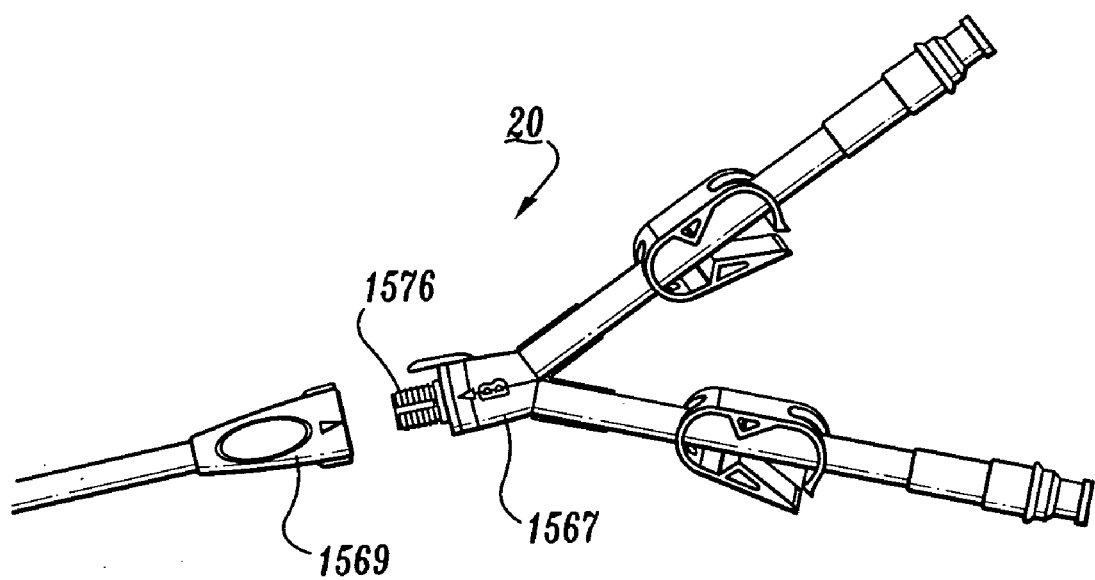
FIG. 26 is an alternate perspective view of the catheter shown in FIG. 25.

In an alternate embodiment, as shown in FIGS. 25 and 26, hub part 1567 and tube part 1569 of catheter 20 are detachable. The detachable components of catheter 20 advantageously reduce bulk. This feature improves patient comfort, facilitates cleaning of hub 532 to reduce the opportunity for infection and allows hub 532 to attach directly to a patient indwelling catheter, thereby minimizing the need for additional accessories/materials. It is contemplated that upon detachment of the components of catheter 20, a cap, self sealing gasket or similar structure may be employed to seal the detached portions of body 522. For assembly of hub part 1567 and tube part 1569, as shown by arrow B in FIG. 25, ports 538, 540 include a barbed outer connector surface 1576 for sealed connection with tube part 1569.

Figure 27:
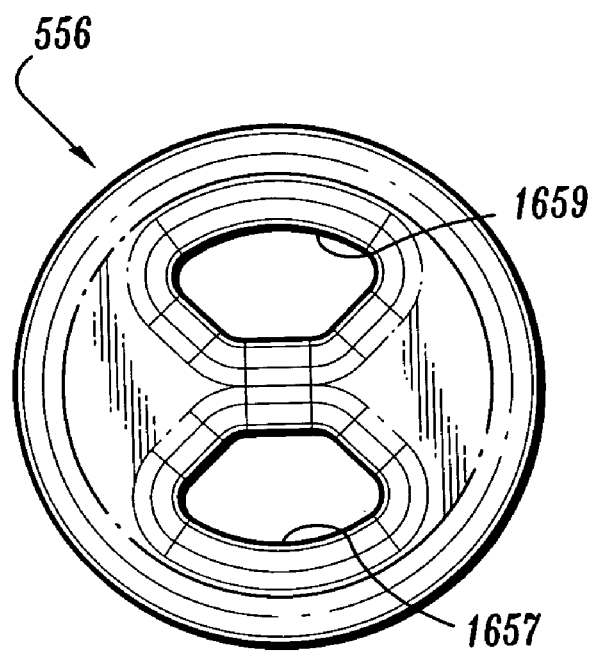
FIG. 27 is a plan view of an alternate embodiment of a washer of the catheter shown in FIG. 15.
Figure 28:
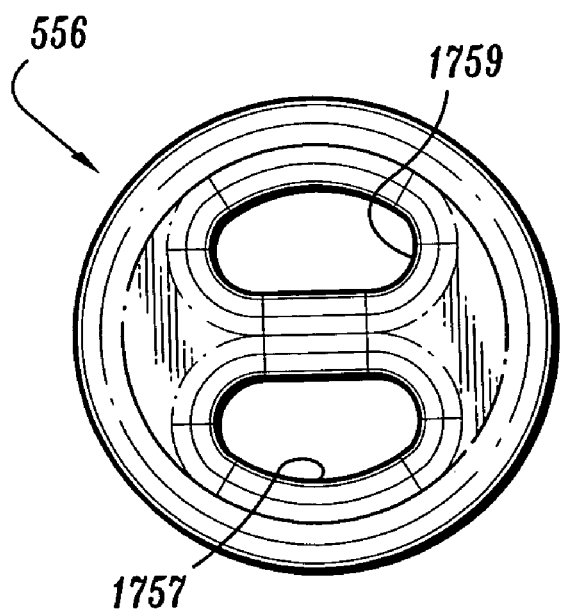
FIG. 28 is a plan view of another alternate embodiment of the washer shown in FIG. 15.

Referring to FIG. 27, an alternate embodiment of washer 556, similar to that described with regard to FIGS. 14–18, is shown. Washer 556 is configured for dual lumen catheter applications of catheter 20 and includes openings 1657, 1659. Openings 1657, 1659 each have a sector configuration that are configured to maximize flow and prevent recirculation during rotation of the ports (described above) to a desired position. As shown in FIG. 28, another alternate embodiment of washer 556 is configured for dual lumen catheter applications of catheter 20 and includes openings 1757, 1759. Openings 1757, 1759 each have a substantially oval configuration.

Figure 29:
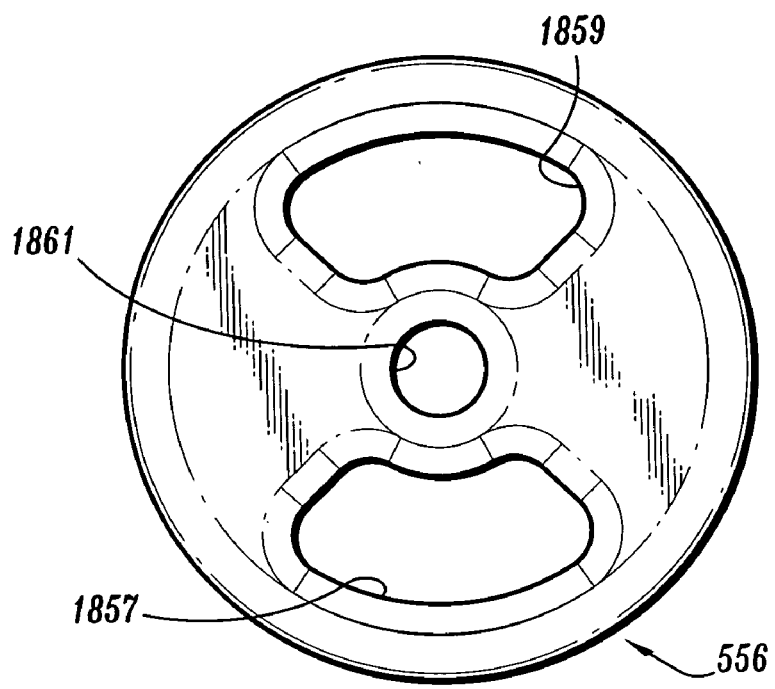
FIG. 29 is a plan view of another alternate embodiment of the washer shown in FIG. 15.
Figure 30:
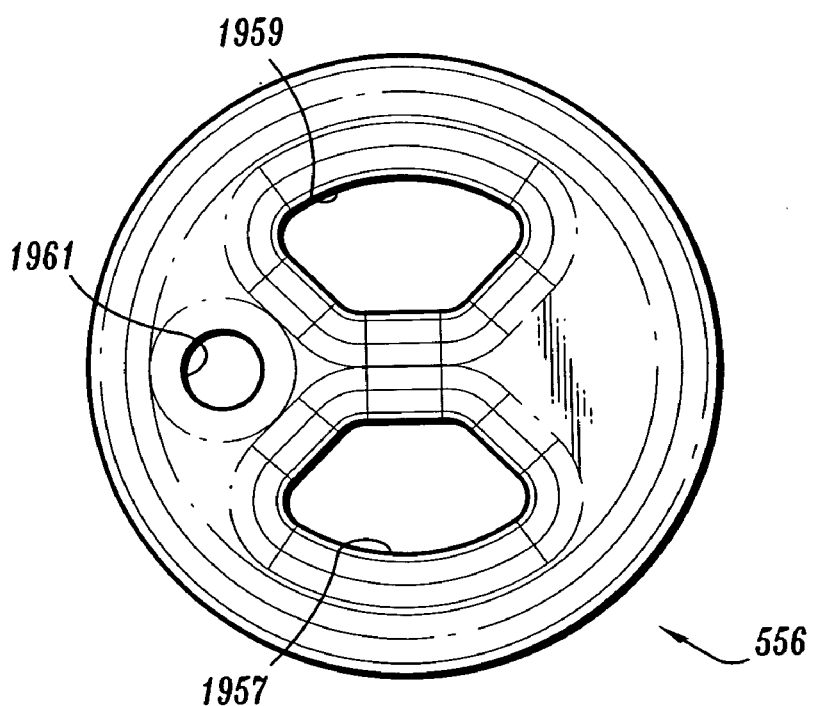
FIG. 30 is a plan view of another alternate embodiment of the washer shown in FIG. 15.

Referring to FIG. 29, another alternate embodiment of washer 556, similar to that described above is shown. Washer 556 is configured for triple lumen catheter applications of catheter 20 and includes openings 1857, 1859 that are configured for reversing flow in catheter 20, as described. Openings 1857, 1859 each have an alternate sector configuration. Washer 556 also includes a central opening 1861 that is disposed for alignment with a corresponding central lumen/conduit. Central opening 1861 is circular, smaller than openings 1857, 1859 and contemplated for infusion applications. It is envisioned that central opening 1861 may have other geometric configurations and be configured for a variety of applications, including reversible flow. As shown in FIG. 30, another alternate embodiment of washer 556 is configured for triple lumen catheter applications of catheter 20 and includes openings 1957, 1959. Openings 1957, 1959 each have a sector configuration. Washer 556 includes an off center opening 1961 that is disposed off the center axis and disposed for alignment with a corresponding lumen/conduit. Off center opening 1961 is circular and smaller than openings 1957, 1959. Off center opening 1961 may be employed for reversible flow, as described, or rotated to an off position.

Figure 31:
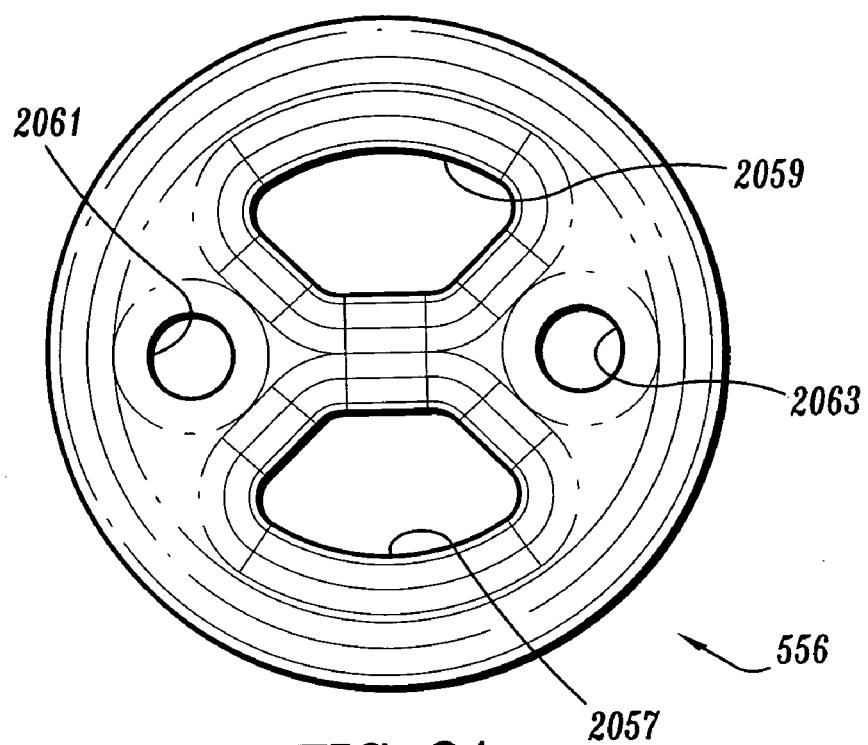
FIG. 31 is a plan view of another alternate embodiment of the washer shown in FIG. 15.

Referring to FIG. 31, another alternate embodiment of washer 556, similar to that described above is shown. Washer 556 is configured for four lumen catheter applications of catheter 20 and includes openings 2057, 2059 that are configured for reversing flow in catheter 20, as described. Openings 2057, 2059 each have a sector configuration. Washer 556 also includes openings 2061, 2063 that are disposed off the center axis and disposed for alignment with corresponding lumens/conduits. Openings 2061, 2063 are circular and smaller than openings 2057, 2059. Openings 2061, 2063 may be employed for reversible flow, as described.

Figure 32:
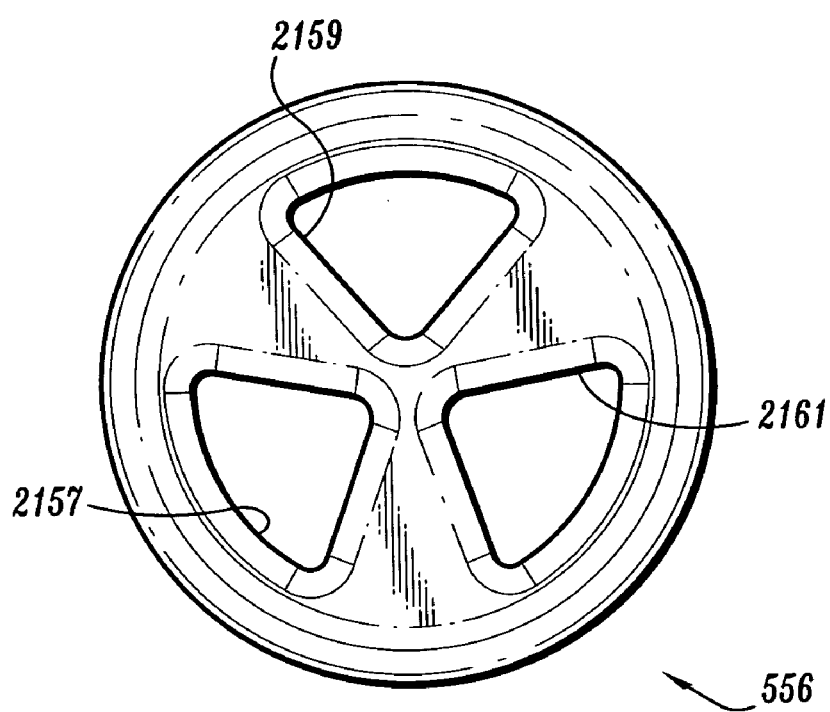
FIG. 32 is a plan view of another alternate embodiment of the washer shown in FIG. 15.

Referring to FIG. 32, another alternate embodiment of washer 556, similar to that described above is shown. Washer 556 is configured for triple lumen catheter applications of catheter 20 and includes openings 2157, 2159 and 2161. Openings 2157, 2159 and 2161 each have a triangular configuration and are disposed for alignment with a corresponding lumen/conduit. Openings 2157, 2159 and 2161 may be employed for reversible flow, as described. It is envisioned that openings 2157, 2159 and 2161 may have other geometric configurations, or that each opening may be alternately configured. In this embodiment, the lumens of catheter 20 may be employed for hemodialysis, infusion and/or withdrawal of fluids.

Figure 33:
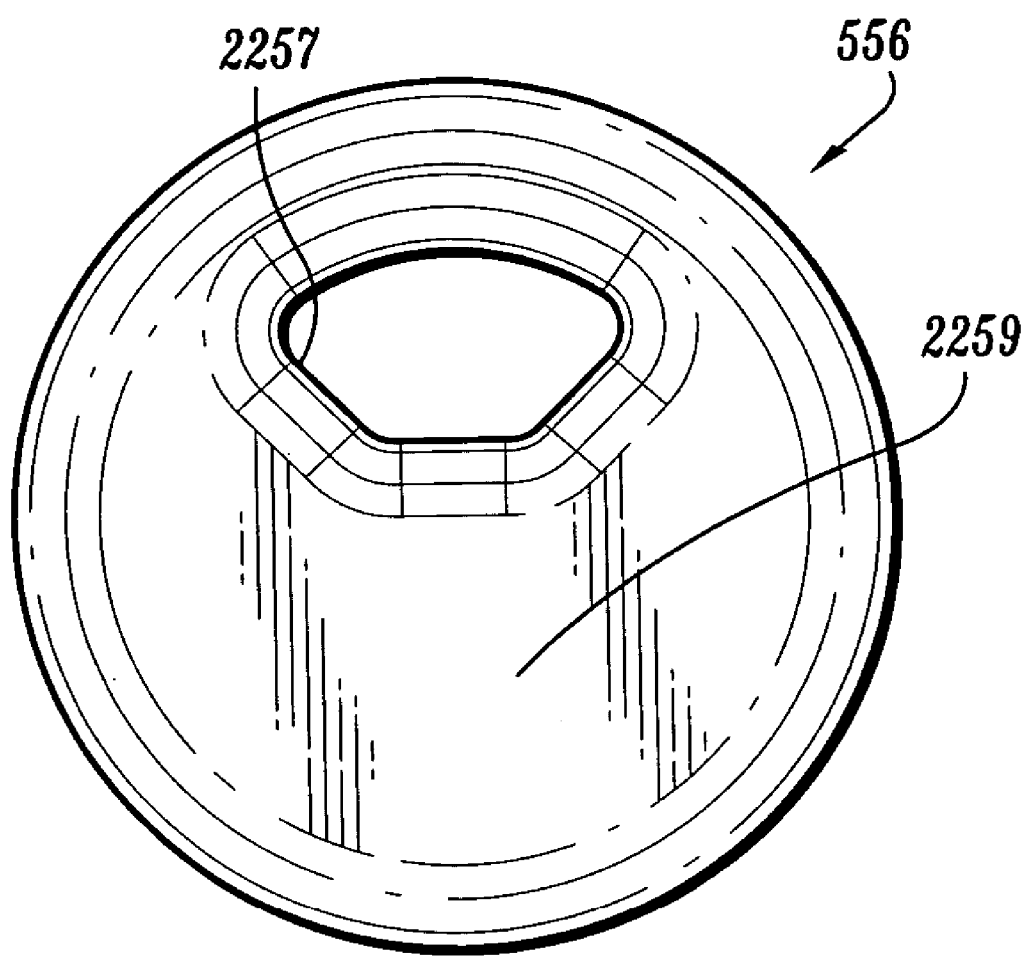
FIG. 33 is a plan view of another alternate embodiment of the washer shown in FIG. 15.

Referring to FIG. 33, another alternate embodiment of washer 556, similar to that described above is shown. Washer 556 is configured for single or multiple lumen catheter applications of catheter 20 and includes an opening 2257 having a sector configuration. Washer 556 also includes a closed surface 2259. In this embodiment, washer 556 is employed to shut off or seal a selected port with closed surface 2259, while facilitating fluid communication with opening 2257 through an alternate port.

It is contemplated that washer 556 may include sealing surfaces that are fabricated from non elastomeric materials, while providing the ability to rotate and provide an adequate seal. For example, washer 556 may include hard, lubricious and smooth surfaces, such as, for example, ceramics, polymer materials or metallic materials. It is further contemplated that the tubular body, and its components, of catheter 20 include antimicrobial agents. For example, the components of hub 532 can treated or impregnated with an antimicrobial compound that will advantageously reduce the incidence of catheter related infections. Such a configuration will reduce contamination of the valve and lumens to reduce infection. The components of catheter 20 can be treated with antimicrobial agents during formation of the components, prior to assembly and subsequent to catheter implantation with a subject. Moreover, antimicrobial treatment could be repeated during use of catheter 20. It is envisioned that catheter 20 may employ a variety of antimicrobial compounds, such as, for example, metal ions, such as silver, antibiotics, chlorhexidine, iodine, EDTA and citrate.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A catheter comprising:
   a tubular body defining a longitudinal axis and having a proximal end and a distal end configured for connection to a subject, the body including a first lumen and a second lumen with a septum disposed therebetween, the tubular body further including a first wall that defines the first lumen and a second wall that defines the second lumen, a portion of the septum extending distally beyond the first lumen and the second lumen, wherein the first wall includes a first wall extension that extends in a spiral configuration from the first lumen about the longitudinal axis and is spaced apart from the portion of the septum,
   the proximal end including a first lumen opening and a second lumen opening formed in a proximal face of the body, the proximal end further including an integral hub having a valve configured for engagement with the proximal face of the body, the hub including a first conduit that extends to a first port of the valve and a second conduit that extends to a second port of the valve,
   the hub being manipulable to rotate the the valves about a longitudinal axis of the body, to establish fluid communication between the lumens and the conduits, wherein the ports are releasably fixed in alignment with the first and second lumen openings during fluid communication.

2. A catheter as recited in claim 1, wherein the distal end of the tubular body is configured for insertion with a subject.

3. A catheter as recited in claim 1, wherein the hub is connected with the valve such that rotation of the hub causes corresponding rotation of the ports.

4. A catheter as recited in claim 1, wherein the first port is aligned with the first conduit and the second port is aligned with the second conduit.

5. A catheter as recited in claim 1, wherein the first port and the second port have a sector configuration.

6. A catheter as recited in claim 1, wherein the valve is rotatable to a first position, such that the first port is aligned with the first lumen and the second port is aligned with the second lumen, and a second position, such that the first port is aligned with the second lumen and the second port is aligned with the first lumen.

7. A catheter as recited in claim 6, wherein the valve is rotatable to a third position, such that the ports are not aligned with the lumens and fluid communication between the conduits and the lumens is prevented.

8. A catheter as recited in claim 6, wherein the valve is releasably lockable with the tubular body in the first position and the second position.

9. A catheter as recited in claim 6, wherein the proximal end of the catheter includes visual indicia of the position of the valve.

10. A catheter as recited in claim 1, further comprising a locking member that fixes the valve with the body to prevent rotation thereof.

11. A catheter as recited in claim 10, wherein the locking member is biased to fix the valve with the body and prevent rotation thereof.

12. A catheter as recited in claim 11, wherein the locking member is axially manipulable to release the valve from locking engagement with the body for corresponding rotation.

* * * * *